US011162192B2

(12) United States Patent
Gopinath et al.

(10) Patent No.: US 11,162,192 B2
(45) Date of Patent: Nov. 2, 2021

(54) MATERIALS AND METHODS RELATING TO SINGLE MOLECULE ARRAYS

(71) Applicants: ARIZONA BOARD OF REGENTS ON BEHALF OF ARIZONA STATE UNIVERSITY, Scottsdale, AZ (US); CALIFORNIA INSTITUTE OF TECHNOLOGY, Pasadena, CA (US)

(72) Inventors: Ashwin Gopinath, Pasadena, CA (US); Paul Rothemund, Pasadena, CA (US); Rishabh Shetty, Tempe, AZ (US); Rizal Hariadi, Phoenix, AZ (US)

(73) Assignees: ARIZONA BOARD OF REGENTS ON BEHALF OF ARIZONA STATE UNIVERSITY, Scottsdale, AZ (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/762,024

(22) PCT Filed: Nov. 30, 2018

(86) PCT No.: PCT/US2018/063345
§ 371 (c)(1),
(2) Date: May 6, 2020

(87) PCT Pub. No.: WO2019/108954
PCT Pub. Date: Jun. 6, 2019

(65) Prior Publication Data
US 2021/0032775 A1    Feb. 4, 2021

Related U.S. Application Data

(60) Provisional application No. 62/593,687, filed on Dec. 1, 2017.

(51) Int. Cl.
*C40B 40/06* (2006.01)
*B82Y 40/00* (2011.01)
(Continued)

(52) U.S. Cl.
CPC ........... *C40B 40/06* (2013.01); *B01J 19/0046* (2013.01); *B01J 2219/00497* (2013.01);
(Continued)

(58) Field of Classification Search
CPC ............................. B01J 19/0046; C40B 40/06
See application file for complete search history.

(56) References Cited

U.S. PATENT DOCUMENTS 6,180,349 B1    1/2001    Ginzinger et al.
6,576,980 B1    6/2003    Shao et al.
(Continued)

FOREIGN PATENT DOCUMENTS

WO    2013/119676 A1    8/2013
WO    2016/144755 A1    9/2016

OTHER PUBLICATIONS

Gopinath et al., ACSNANO, 2014, vol. 8, No. 12, Supplemental Information (Year: 2014).*
(Continued)

*Primary Examiner* — Kaijiang Zhang
*Assistant Examiner* — Taryn Kimberly Wood
(74) *Attorney, Agent, or Firm* — Michael Best & Friedrich LLP

(57) ABSTRACT

Embodiments of the present disclosure relate generally to single molecule arrays. More particularly, the present disclosure provides materials and methods for generating single molecule arrays using bottom-up self-assembly processes. Materials and methods of the present disclosure can be used to generate single molecule arrays with nanoapertures (e.g.,
(Continued)

zero mode waveguides) and for carrying out rapid, point-of-care biomolecule detection and quantification.

16 Claims, 14 Drawing Sheets

(51) Int. Cl.
   *B01J 19/00* (2006.01)
   *B82Y 5/00* (2011.01)
(52) U.S. Cl.
   CPC ........... *B01J 2219/00596* (2013.01); *B01J 2219/00612* (2013.01); *B01J 2219/00722* (2013.01); *B82Y 40/00* (2013.01)

(56) References Cited

U.S. PATENT DOCUMENTS

| | | |
|---|---|---|
| 6,917,726 B2 | 7/2005 | Levene et al. |
| 8,318,508 B2 | 11/2012 | Mirkin et al. |
| 8,323,686 B2 | 12/2012 | Mirkin et al. |
| 8,323,888 B2 | 12/2012 | Mirkin et al. |
| 8,425,653 B2 | 4/2013 | Mirkin et al. |
| 8,507,200 B2 | 8/2013 | Mirkin et al. |
| 8,512,946 B2 | 8/2013 | Mirkin et al. |
| 8,906,831 B2 | 12/2014 | Eid et al. |
| 9,013,689 B2 | 4/2015 | Reinhard et al. |
| 2002/0053532 A1 | 5/2002 | Quake et al. |
| 2012/0028342 A1 | 2/2012 | Ismagilov et al. |
| 2012/0225251 A1 | 9/2012 | Mirkin et al. |
| 2012/0244230 A1 | 9/2012 | Mirkin et al. |
| 2012/0269730 A1 | 10/2012 | Mirkin et al. |
| 2012/0277114 A1 | 11/2012 | Duffy et al. |
| 2012/0277283 A1 | 11/2012 | Mirkin et al. |
| 2012/0282186 A1 | 11/2012 | Mirkin et al. |
| 2012/0283316 A1 | 11/2012 | Mirkin et al. |
| 2012/0288935 A1 | 11/2012 | Mirkin et al. |
| 2012/0295029 A1 | 11/2012 | Mirkin et al. |
| 2012/0297509 A1 | 11/2012 | Mirkin et al. |
| 2013/0034599 A1 | 2/2013 | Thaxton et al. |
| 2013/0040856 A1 | 2/2013 | Mirkin et al. |
| 2013/0078740 A1 | 3/2013 | Miller et al. |
| 2013/0101512 A1 | 4/2013 | Mirkin et al. |
| 2013/0123333 A1 | 5/2013 | Mirkin et al. |
| 2013/0178610 A1 | 7/2013 | Mirkin et al. |
| 2013/0240356 A1 | 9/2013 | Wanunu et al. |
| 2017/0051338 A1 | 2/2017 | Manetto |

OTHER PUBLICATIONS

Rothemund, Nature, 2006, 440:16, 297-302 (Year: 2006).*
Dirks et al., PNAS, 2004, 101:43, 15275-15278 (Year: 2004).*
Beer et al., "On-chip, real-time, single-copy polymerase chain reaction in picoliter droplets," Anal. Chem., 2007, 79(22):8471-8475.
Choi et al., "Next-Generation in Situ Hybridization Chain Reaction: Higher Gain, Lower Cost, Greater Durability," ACS Nano, 2014, 8(5): 4284-4294.
Colson et al., "Nanosphere lithography: A powerful method for the controlled manufacturing of nanomaterials," J. Nanomater., 2013, vol. 2013, Article ID 948510, 19 pages.
Dai et al., "Optical imaging of individual biomolecules in densely packed clusters," Nat. Nanotechnol., 2016, 11(9):798-807.
Dirks et al., "Triggered amplification by hybridization chain reaction," Proc. Natl. Acad. Sci. U. S. A., 2004, 101(43):15275-15278.
Douglas et al., "Rapid prototyping of 3D DNA-origami shapes with caDNAno," Nucleic Acids Res, 2009, 37(15):5001-5006.
Eid et al., "Real-time DNA sequencing from single polymerase molecules," Science, 2009, 323(5910):133-138.
Foquet et al., "Improved fabrication of zero-mode waveguides for single-molecule detection," J. Appl. Phys., 2008, 103:1-9.
Fu et al., "A microfabricated fluorescence-activated cell sorter," Nat. Biotechnol., 1999, 17(11):1109-11.
Gopinath et al., "Engineering and mapping nanocavity emission via precision placement of DNA origami," Nature, 2016, 535(7612):401-405.
Gopinath et al., "Optimized assembly and covalent coupling of single-molecule DNA origami nanoarrays," ACS Nano, 2014, 8(12):12030-12040.
Heid et al., "Real time quantitative PCR," Genome Res, 1996, 6(10):986-994.
Heucke et al., "Placing individual molecules in the center of nanoapertures," Nano Lett, 2014, 14:391-395 (Available online Jun. 2013).
Hindson et al., "High-throughput droplet digital PCR system for absolute quantitation of DNA copy number," Anal. Chem., 2011, 83(22):8604-8610.
Hulteen et al., "Nanosphere lithography: A materials general fabrication process for periodic particle array surfaces," J. Vac. Sci. Technol. A Vacuum, Surfaces, Film., 1995, 13(3):1553-1558.
International Search Report and Written Opinion for Application No. PCT/US2018/063345 dated Feb. 21, 2019 (26 pages).
Jungmann et al., "Quantitative super-resolution imaging with qPAINT using Transient Binding Analysis," Nat. Methods, 2016, 13(5):439-442.
Kershner et al., "Placement and orientation of individual DNA shapes on lithographically patterned surfaces," Nat. Nanotechnol., 2009, 4(9):557-561.
Korlach et al., "Selective aluminum passivation for targeted immobilization of single DNA polymerase molecules in zero-mode waveguide nanostructures," Proc. Natl. Acad. Sci. U. S. A., 2008, 105(4):1176-1181.
Levene et al., "Zero-mode waveguides for single-molecule analysis at high concentrations," Science, 2003, 299(5607):682-686.
Li et al., "Engineering the spatial selectivity of surfaces at the nanoscale using particle lithography combined with vapor deposition of organosilanes," ACS Nano, 2009, 3(7):2023-2035.
Munroe et al.,"Third-generation sequencing fireworks at Marco Island," Nat. Biotechnol., 2010, 28(5):426-428.
Nallur et al., "Signal amplification by rolling circle amplification on DNA microarrays," Nucleic Acids Res., 2001, 29(23):e118.
Schnitzbauer et al., "Super-resolution microscopy with DNA-PAINT," Nat. Protoc., 2017, 12(6):1198-1228.
Shen et al., "Plasmonic nanostructures through DNA-assisted lithography," Science Advances, 2018, 4(2):1-7.
Sims et al., "Fluorogenic DNA sequencing in PDMS microreactors," Nat. Methods, 2011, 8(7):575-580.
Teng et al., "Fabrication of nanoscale zero-mode waveguides using microlithography for single molecule sensing," Nanotechnology, 2012, 23(45):455301.
Thorsen et al., "Microfluidic Large-Scale Integration," Science, 2002, 298(5593):580-4.
Vogel et al., "A convenient method to produce close- and non-close-packed monolayers using direct assembly at the air-water interface and subsequent plasma-induced size reduction," Macromol. Chem. Phys., 2011, 212(16):1719-1734.
Zhao et al., "Lab-on-a-chip technologies for single-molecule studies," Lab Chip, 2013, 13(12):2183-98.

\* cited by examiner

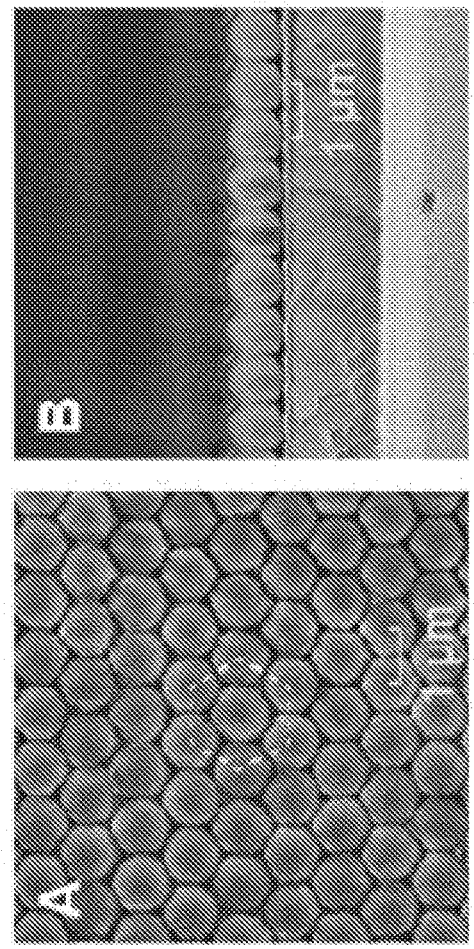
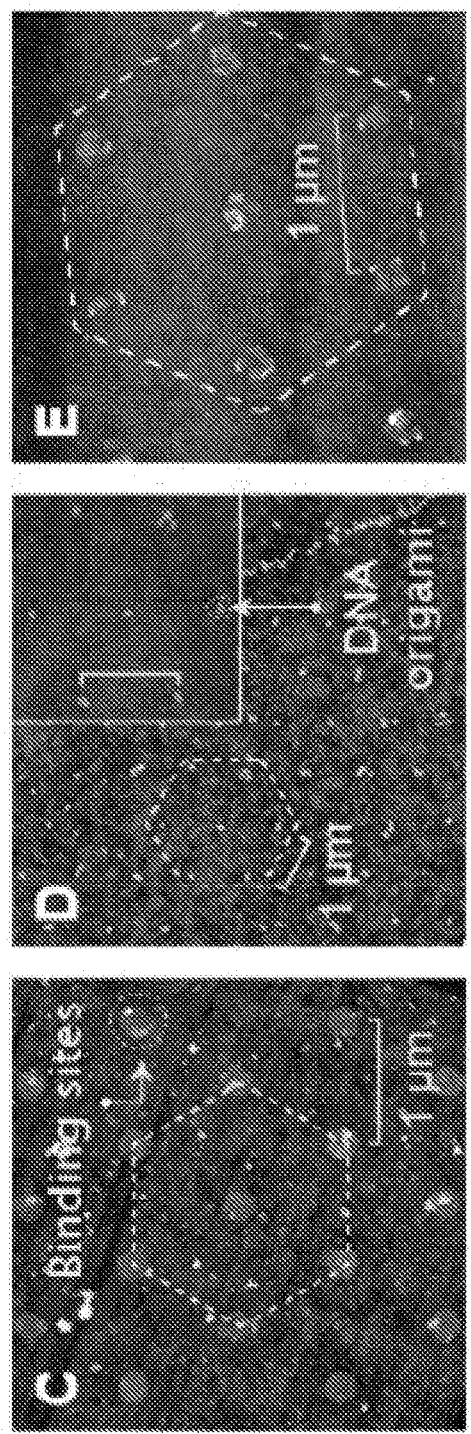
FIGS. 2A-2E

MATERIALS AND METHODS RELATING TO SINGLE MOLECULE ARRAYS

CROSS-REFERENCE TO RELATED APPLICATIONS

This application claims the benefit of U.S. Provisional Patent Application No. 62/593,687, filed on Dec. 1, 2017, the entire content of which is fully incorporated herein by reference.

STATEMENT REGARDING FEDERALLY SPONSORED RESEARCH OR DEVELOPMENT

This invention was made with government support under Grant No. CCMI1636364 awarded by the National Science Foundation and Grant Nos. N00014-14-1-0702 & N00014-17-1-2610 awarded by the Office of Naval Research. The government has certain rights in the invention.

FIELD

Embodiments of the present disclosure relate generally to single molecule arrays. More particularly, the present disclosure provides materials and methods for generating single molecule (e.g., DNA origami) arrays with bottom-up self-assembly processes for rapid, point-of-care biomolecule detection and quantification.

BACKGROUND

Nanotechnology based on the use of artificial nucleic acids (e.g., DNA origami) is modular, spatially-programmable, and capable of organizing various biological and non-biological molecules of interest. Nanofabricated devices, traditionally hindered by stochastic loading of active, single-molecule components, can benefit significantly from the precise positional control offered by DNA nanostructures. The statistical (Poisson-) limitation placed on single-molecule localization when realized through conventional top-down technologies can be overcome by an origami-based platform. This can facilitate the development of biophysical devices aimed at increasing the throughput and efficiency of single-molecule experiments. The biosensing capability of DNA origami breadboards can be exploited by conjugating disease-specific linker strands to them for precise targeting, in situ amplification, and quantitative measurements of nucleic-acid-based disease particles.

The current gold standard for quantitative nucleic acid detection is qPCR, which is limited by its equipment/reagent cost, and the need for thermal cycling. With regards to its extension to an "on-chip" in situ device platform, qPCR is severely limited by the diffusion of products into solution. High-throughput DNA microarray technology on the other hand suffers from an inherent limitation: while it is capable of sensitive in situ detection of microbe presence (using longer probes), it fails to quantify viral loads. Several in situ isothermal approaches compatible with product localization (while demonstrating excellent sensitivity), such as Hybridization Chain Reaction and Rolling Circle Amplification, exhibit the potential to overcome these limitations. DNA nanotechnology enables the self-assembly of origami nanostructures (capable of carrying active components) into 2D and 3D conformations. By extension, origami placement enables these nanostructures to serve as substrates for in situ isothermal amplification of bound nucleic acid targets. It thereby retains the advantages of highly sensitive isothermal amplification while facilitating broader functionality and addressability through precise origami placement on a chip-based platform.

The programmable placement of functionalized DNA origami nanostructures on addressable substrates accentuates their utility as a portable, nucleic-acid-based digital assay platform for detecting biomarkers at ultra-low concentrations. The unique programmability of DNA origami has the potential to make the proposed biosensing platform a powerful research and diagnostic tool in the academic and clinical settings.

SUMMARY

Embodiments of the present disclosure relate generally to a single molecule array that includes an activated silanol-enriched glass substrate, a organosilane base layer deposited onto the glass substrate, wherein the organosilane base layer comprises a plurality of regularly spaced binding sites, and an artificial nucleic acid nanostructure layer comprising a plurality of individual nucleic acid molecules bound to silanol groups on the glass substrate within the plurality of regularly spaced binding sites. In accordance with these embodiments, the binding sites have diameters formed by a plurality of regularly spaced removable nanospheres deposited on and in contact with the glass substrate prior to application of the organosilane base layer.

Embodiments of the present disclosure also relate generally to a single molecule array that includes an activated silanol-enriched glass substrate a metallic base layer deposited onto the glass substrate, wherein the metallic base layer comprises a plurality of regularly spaced nanoapertures, and an artificial nucleic acid nanostructure layer comprising a plurality of individual nucleic acid molecules contained within each nanoaperture and bound to silanol groups on the glass substrate, wherein the nanoapertures have diameters formed by a plurality of regularly spaced removable nanospheres deposited on and in contact with the glass substrate prior to application of the metallic base layer. In accordance with these embodiments, the metallic layer can include at least one of aluminum, silver, gold, chromium, or combinations thereof.

Embodiments of the present disclosure also relate generally to a method for manufacturing a single molecule array that includes depositing a plurality of removable nanospheres onto an activated silanol-enriched glass substrate, depositing an organosilane base layer onto the glass substrate and the plurality of nanospheres, removing the plurality of nanospheres to form a plurality of binding sites in the organosilane base layer in regions where the plurality of nanospheres contacted the glass substrate, and depositing an artificial nucleic acid nanostructure layer comprising a plurality of individual nucleic acid molecules onto the organosilane base layer, wherein the plurality of individual nucleic acid molecules are contained within the plurality of binding sites, and are bound to silanol groups on the glass substrate.

Embodiments of the present disclosure also relate generally to a method of performing points accumulation for imaging in nanoscale topology (PAINT), in situ nucleic acid amplification through hybridization chain reaction (HCR), or hybridization chain reaction (HCR)-based biosensing for detecting or diagnosing a disease target using the single molecule array described above.

BRIEF DESCRIPTION OF THE DRAWINGS

FIGS. 2A-2E include representative images from various stages of a single molecule array fabrication process, including benchtop, cleanroom-free DNA origami placement. Scanning electron microscopy (SEM) (FIG. 2A) and high-tilt SEM (FIG. 2B) images demonstrate hexagonal close-packing (HCP) of a polystyrene nanosphere monolayer; atomic force microscopy (AFM) images demonstrate hexagonal arrays of binding sites (FIG. 2C); DNA origami nanostructures on a PEG-silane background are demonstrated with (inset) a hexagonal arrangement of DNA origami nanostructures; and hexagonal arrangement and multiple DNA origami molecules binding to an HMDS-passivated substrate is demonstrated (FIG. 2E).

FIG. 3A includes an image of 30,000 integrated fluorescence frames collected on a super-resolution microscope; FIG. 3B includes a section of the array showing multiple hexagonal arrangements of DNA origami; and FIG. 3C) includes representative 4×3, 20-nm grids of linker strands unraveled post-Picasso processing on a dataset collected using traditional PAINT protocol.

FIG. 5E demonstrates >95% single-molecule occupancy for the ZMW array (e.g., single DNA polymerase per ZMW).

(FIG. 7B). Experimental results highlighting optimized single, circular origami placement on nanosphere-defined "binding" sites for digital assays. FIG. 7C shows representative images from various stages of a single molecule array fabrication process, including benchtop, cleanroom-free DNA origami placement. Scanning electron microscopy (SEM) and high-tilt SEM images demonstrate hexagonal close-packing (HCP) of a polystyrene nanosphere monolayer; atomic force microscopy (AFM) images demonstrate hexagonal arrays of binding sites; DNA origami nanostructures on a PEG-silane background are demonstrated with (inset) a hexagonal arrangement of DNA origami nanostructures; and hexagonal arrangement and multiple DNA origami molecules binding to an HMDS-passivated substrate is demonstrated.

FIG. 8A shows Cross-sectional Scanning Electron Micrographs (top) and corresponding Atomic Force Micrographs (bottom) of nanospheres, and their corresponding binding sites. FIG. 8B shows ~94% linear dependence of binding site size on nanosphere diameter. FIG. 8C shows Mean occupancy percentage of 0, 1, or more than one origami in binding sites as a function of nanosphere diameter demonstrating non-Poisson statistics of single molecule binding. FIG. 8D shows Nanoarray patterning facilitated by an automated washing step using a peristaltic pump to mitigate manual error propagation. Scale bars are 500-nm.

FIG. 10A shows a schematic representation of the isothermal amplification process (Hybridization Chain Reaction. FIG. 10B shows optimal surface passivation through competitive excess strand binding (~200× excess) for minimal false positives. FIG. 10C shows serial dilution of synthetic target species indicating a ~10-100 pM limit of detection. FIG. 10D shows detection of an amplification reaction using a low-cost (~$1300) microscope (at 10 nM target concentration) for assay portability. Scale bars are 1000-nm.

DETAILED DESCRIPTION

Figures 1A, 1B, 1C, 1D, 1E:
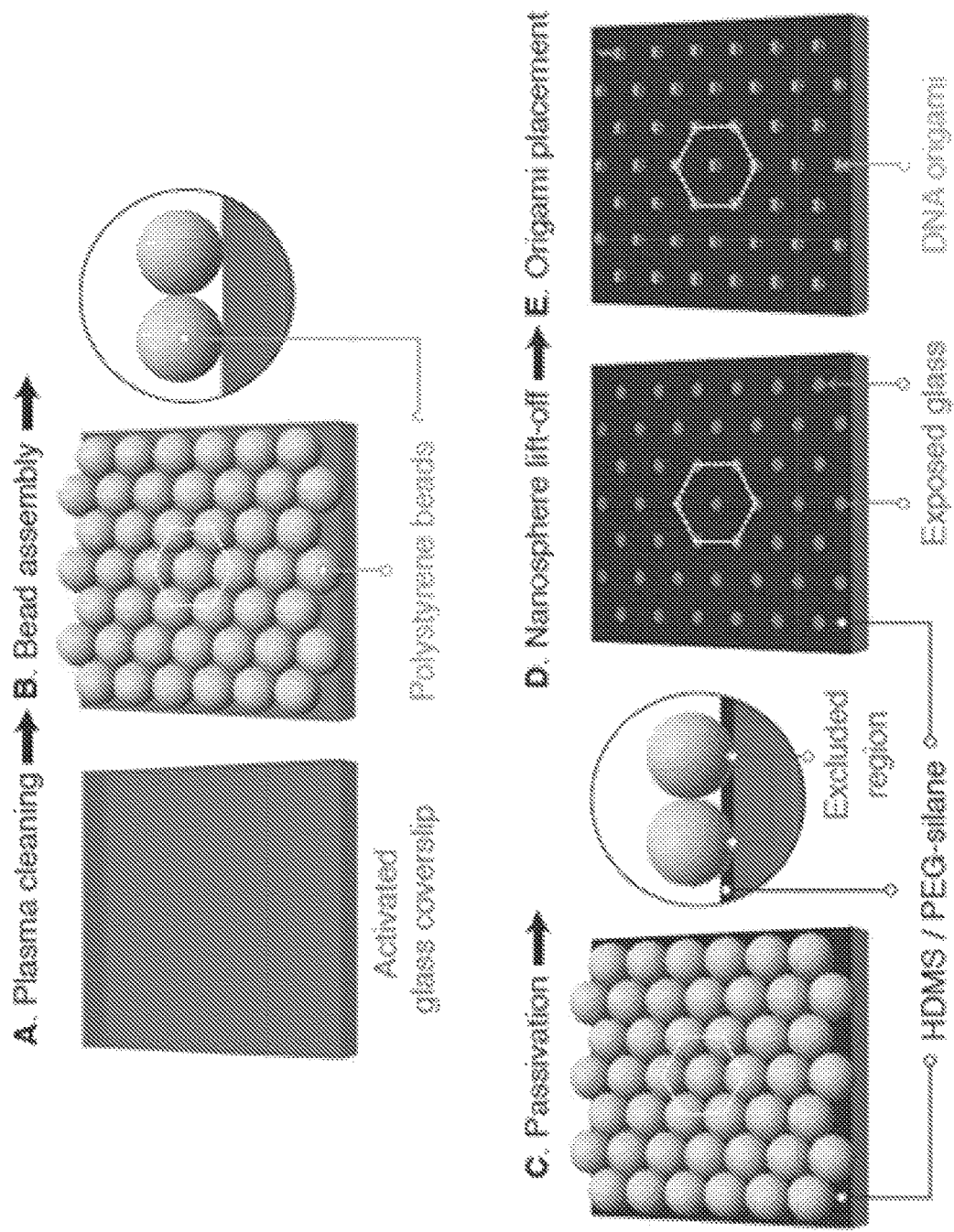
FIGS. 1A-1E include representative schematics of an exemplary workflow for single molecule array fabrication, including nanosphere patterning (NP) processes and DNA origami deposition. Glass coverslips are activated in a plasma cleaner (FIG. 1A), followed by nanosphere monolayer self-assembly (FIG. 1B), surface passivation (FIG. 1C), nanosphere lift-off (FIG. 1D), and DNA origami placement (FIG. 1E).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The use of the terms "a" and "an" and "the" and "at least one" and similar referents in the context of describing the invention (especially in the context of the following claims) are be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA; or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Polypeptide" and "isolated polypeptide" as used herein refers to a polymer of amino acids or amino acid derivatives that are connected by peptide bonds. An isolated polypeptide is a polypeptide that is isolated from a source. An isolated polypeptide can be at least 1% pure, at least 5% pure, at least 10% pure, at least 20% pure, at least 40% pure, at least 60% pure, at least 80% pure, and at least 90% pure, as determined by one or more protein biochemistry techniques (e.g., SDS-PAGE).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Treat," "treated," or "treating," as used herein, refer to a therapeutic method wherein the object is to slow down (lessen) an undesired physiological condition, disorder or disease, or to obtain beneficial or desired clinical results. In some aspects of the present disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof, or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Before any embodiments of the present disclosure are explained in detail, it is to be understood that the present disclosure is not limited in its application to the details of construction and the arrangement of components set forth in the following description or illustrated in the accompanying drawings. The present disclosure is capable of other embodiments and of being practiced or of being carried out in various ways.

Other aspects of the invention will become apparent by consideration of the detailed description and accompanying drawings.

Embodiments of the present disclosure relate generally to single molecule arrays. More particularly, the present disclosure provides materials and methods for generating single molecule arrays using bottom-up self-assembly processes. Materials and methods of the present disclosure can be used to generate single molecule arrays with nanoapertures (e.g., zero mode waveguide nanoapertures) for carrying out rapid, point-of-care biomolecule detection and quantification.

Programmed DNA origami placement in highly ordered grids is a key technology that enables the integration of these nanostructures with optically addressable substrates. Currently, the ability to fabricate single-origami grids on substrates relies on nanofabrication approaches such as Electron-Beam Lithography (EBL), an expensive technique which requires specialized training and is tedious to execute. Application of a Nanosphere Patterning (NP)-based approach can recapitulate the nanometer-scale precision achievable with EBL-based origami placement, while making it a cleanroom-free approach, easily achievable on a basic laboratory benchtop. This type of fabrication technique, as applied to DNA origami placement, can be fundamental as a bottom-up alternative for building devices such as Zero Mode Waveguides (ZMWs) which are traditionally EBL-nanofabricated, and Poisson-limited. Zero Mode Waveguides are metal nanoapertures that confine the observation volume to a few zeptoliters ($10^{-21}$ L) thereby attaining unprecedented Signal to Noise Ratios (SNR) and facilitating high-throughput single-molecule experiments.

Through the development of a cleanroom-free Nanosphere Patterning platform, DNA origami placement technology can be extended to the low-cost, bottom-up fabrication of Zero Mode Waveguides for high-throughput DNA sequencing studies.

A bottom-up approach based on NP can be easily applied to the fabrication of ZMWs by binding a single nanosphere to each origami, depositing metal, and finally, dissolving the nanospheres. The final device is a grid of ZMW metal nanoapertures, each with a "pre-loaded/built-in" single origami capable of recruiting additional molecules of interest at physiologically relevant concentrations. This enables high-throughput single molecule experiments to be run in parallel at a significantly higher efficiency of single-molecule loading than has previously been possible in ZMWs. Thus, the NP technique not only overcomes the single-molecule occupancy barrier, but by using these single-molecules (e.g., DNA origami) as baseplates for ZMW device fabrication from the bottom-up, also drives the practical usage of the device up to >95%. Embodiments of the present disclosure challenge the convention of using DNA origami nanostructures as the molecules to be loaded into ZMWs. Instead, the present disclosure demonstrates the use of DNA origami nanostructures as building blocks for bottom-up ZMW fabrication, consequently building them into the ZMWs to overcome Poisson statistics.

Single-molecule experiments allow direct visualization and measurement of dynamics without the need for synchronization as is commonplace in bulk experiments. Often, for single-molecule experiments in a Total Internal Reflection Fluorescence (TIRF) setup, for example, spatial constraining of a system through surface immobilization can be achieved through biotin-streptavidin or similar chemistry. However, even with TIRF, optical observation of single-molecule dynamics has been limited by the need to dilute fluorophore concentrations down to the pM or nM concentrations for isolation of individual molecules.

Zero Mode Waveguides (ZMWs) are unique tools that constrict the observation volume three orders of magnitude more than does traditional TIRF. They therefore lend themselves favorably to single molecule experiments at μM-mM concentrations of ligands at microsecond temporal resolution. These metal nanoapertures can confine the volume of fluorescence excitation and provide unprecedented Signal to Noise Ratio (SNR) for single-molecule imaging. Genomic processes, and in particular, long read-length, DNA sequencing (at 2-4 bases/sec) have been enhanced by the use of ZMW devices.

While they have been successful commercially, these devices have found it hard to be decoupled from the cleanroom, and expensive equipment for their fabrication. This is the prominent reason why, despite their obvious utility, they have yet to become commonplace in single-molecule biophysics research laboratories around the world. Additionally, top-down stochastic loading and observation of single molecules in ZMWs is, like any probabilistic approach, Poisson limited (e.g., limited to 37% single-molecule occupancy). This problem stems from the nanotechnological challenge of integrating top-down production/fabrication with the bottom-up molecular world of chemistry and biology.

The utility of ZMWs in single-molecule experiments, including for example, single polymerase for DNA sequencing, can involve one molecule per ZMW. Random deposition and immobilization processes for single-polymerase binding, and consequent sequencing will always be limited by Poisson statistics for single-molecule occupancy at 37%.

That is, unless significantly altered (e.g., being built from the bottom-up), only 37% of currently-available ZMWs can actually be utilized for experiments.

DNA nanotechnology relies on self-assembly in solution, and as such, immobilization of these nanostructures for single-molecule recruitment in ZMWs has traditionally only been achievable via top-down loading and biotin-streptavidin or similar conjugation. Again, only ~60% single-molecule occupancy (in the case of self-assembled origami structures) is expected in the best case scenario. The use of DNA origami placement technology involves DNA nanostructures compatible with traditional fabrication and microscopy substrates such as silicon, silicon dioxide, and silicon nitride. This technique relies on creation of lithographically-defined binding sites at a preset distance from each other, forming a spatially ordered 2D grid. Electrostatic or covalent coupling with a treated substrate enables single origami placement with nanometer precision exclusively in the binding sites. Importantly, by virtue of size-matching the binding sites to origami dimensions and optimizing experimental parameters, such placement can include up to approximately 95% single-origami binding on a given substrate. This overcomes the Poisson limit imposed on traditional top-down loading physics, as well as previously mentioned origami nanoadapter techniques.

Placement technology is ideally suited to high throughput, massively parallel single-molecule experiments, and would increase the efficiency of DNA sequencing in ZMWs. For example, since the presence of more than one polymerase will lead to dephasing such that tracking becomes difficult and the sequence information is lost, a single DNA polymerase molecule can be immobilized at the glass bottom of a ZMW. This polymerase processes a DNA fragment and adds complementary deoxyribonucleoside triphosphates (dNTPs) in solution to form double-stranded DNA. However, in this case, fluorophores are linked to the terminal phosphate moiety of each dNTP (e.g., when a new free-floating dNTP is incorporated by the polymerase a fluorescent signal emission ensues). When DNA polymerase catalyzes the phosphodiester bond formation, resulting in the release of the bound fluorophore, the fluorescent pulse is terminated.

The processivity of the DNA polymerase gives rise to a time trace of fluorescent events, each event relating to the conclusion of a specific dNTP incorporation, thereby enabling real-time DNA sequencing. The process of immobilizing DNA polymerase to the bottom of ZMWs, however, is Poisson-limited. Binding a polymerase to each single patterned origami molecule will ensure higher than 95% occupancy and thus, higher throughput for real-time sequencing applications. DNA origami's ability to bind various functionalized biological and non-biological molecules makes it a useful building block for fabrication of bottom-up device platforms. Currently, Electron-Beam Lithography (EBL) forms the backbone of DNA origami placement technology through binding site creation. However, similar to the issue with ZMW fabrication, EBL requires specialized training and expensive equipment, which is not always a viable option in the research setting. A simpler, cleanroom-free, and hence, widely accessible origami placement technique can be envisioned via a modified nanosphere lithography approach described in the present disclosure as Nanosphere Patterning (NP). Using a close-packed crystalline monolayer of self-assembled nanospheres as a sacrificial mask, perfectly ordered, easily modifiable, and optically resolvable grids of binding sites on the order of approximately 140 million/cm$^2$ can be created via selective surface modification. FIGS. 4A-4E depicts a workflow for NP-based origami placement at non-Poisson limited single origami occupancy.

By virtue of its optical addressability, even without the fabrication of ZMWs, DNA origami placement can serve as a nucleic acid-based quantitative disease-detection platform, as described herein. Immobilized DNA origami can host linker/probe strands capable of binding disease-specific DNA/RNA from a given sample. Thereafter, in situ amplification of bound viral DNA/RNA can enable an ultrasensitive quantitative readout. DNA microarrays do not quantify target molecules as accurately or efficiently as NP-origami array based technology. NP-based programming sets the pitch between origami at a value well above the diffraction limit to approximately 1 μm. Fluorescence detection will allow straightforward counting of bound molecules (amplified or unamplified) with each fluorescent spot indicating exactly one target molecule binding event. Complex image processing techniques are required to attempt to resolve individual detection spots on a DNA microarray, limiting its quantitative ability. Using NP to set the spatial separation between individual origami to well over the diffraction limit facilitates accurate quantification of bound nucleic acid targets and the quantitative determination of copy numbers in a given sample volume with simplified detection optics. The detection sensitivity of such a platform is similar to conventional qPCR's, while having significant advantages over it, which include but are not limited to, product immobilization, isothermal amplification, and on-chip compatibility. By simplifying detection optics, the entire device can be made portable and can be used; for example, as a quantitative, point-of-care (POC) NP-platform for disease-detection through a smartphone-based imaging module.

Using colloidal self-assembly to organize DNA origami. Self-assembly of a monolayer of nanospheres can be used to create binding sites for single origami (e.g., ~80 nm×60 nm, rectangular), and surface passivation enables programmable binding. The monolayer can be created using Langmuir-Blodgett type deposition, controlled evaporation, or 3-D printer based tilted deposition. Binding site diameter and pitch can be determined by the nanosphere diameter chosen, and the effectiveness of surface passivation. PEG-silane-, or Hexamethyldisilazone (HMDS)-based background passivation, for example, will be used for creating single-origami-binding sites. Alternatively, carboxysilane (CTES, CDAP) can also be used for low magnesium concentration binding. The footprints of nanospheres (e.g., binding sites for DNA origami) are the only sites that remain non-passivated, and consequently bind DNA origami nanostructures. Traditionally, nanometer scale-precision origami placement has been achieved using Electron-Beam Lithography (EBL) a technique which can be prohibitively expensive, and requires extensive training. A self-assembly approach such as Nanosphere Patterning (NP) described herein is compatible with bench-top fabrication of chip-to-wafer scale high-density ordered arrays, for single molecule positioning.

Large origami to allow organization on larger patches. The present disclosure includes DNA origami larger than traditional origami that can be self-assembled using a single scaffold strand by using four scaffolds and annealing four separate quadrants before linking them together to form larger, approximately 160×160 nm DNA origami nanostructures. This enables the use of larger nano/microsphere sizes to create binding sites, and also ensures single-origami-binding. The utility of this is two-fold: first, a larger surface area on individual origami to attach biomolecules-of-interest, conducive to multiplexing; and second, the origami can be more spatially separated from each other, requiring basic fluorescence microscope setups for optical resolution of signals.

Multi-level colloidal self-assembly to reduce size patch, Once a periodic array of binding sites has been created using NP and surface passivation, electrostatic binding of microspheres can be facilitated under the right pH conditions. Another round of surface passivation can enable an iterative reduction in the binding site diameter; each corresponding site depending on the size of microspheres used for patterning in that step. This results in the establishment of a multi-level paradigm of iterative NP for reduction of binding site bounds.

Positioning DNA, RNA, Proteins. DNA origami, owing to its inherent Watson-Crick base pair architecture, can be exploited to host several linker strands capable of recruiting biomolecules of interest through complementary nucleotide-binding. For example, as described herein, any molecule/ligand that can be coupled to DNA, from small proteins to large aptamers, can be incorporated into a DNA origami macromolecule in a programmable, accessible, and addressable fashion. This makes DNA origami nanostructures multi-functional breadboards. DNA origami can also be used for biosensing capability by functionalizing them with complementary strand sequences for targeted nucleic-acid, and protein-based disease, and biomarker detection, for example.

Amplification of binding events using HCR, enzymatic amplification (terminal transferase), PCR using PDMS wells. Once bound to "probe" sequences on DNA origami, in situ amplification using an enzyme-free isothermal approach such as Hybridization Chain Reaction (HCR) can enable the detection of a fluorescent optical signal from the bound product. Rolling Circle Amplification (RCA) is another in situ amplification technique that can be utilized. An enzyme-assisted nucleic-acid based amplification approach is using terminal transferase, specifically enabling amplification, and counting triggered by a binding event. DNA sequencing in PDMS microreactors, and its natural extension to clonal amplification by emulsion PCR can be achieved with SMRT sequencing. The NP method can be used for fabricating ZMWs from the bottom-up, as described herein.

EXAMPLES

The following examples are illustrative of disclosed methods. In light of the present disclosure, those of skill in the art will recognize that variations of these examples and other examples of the disclosed method would be possible without undue experimentation.

Embodiments of the present disclosure related to methods of fabricating single molecule arrays including DNA origami placement with nanoscale precision. Embodiments of the present disclosure involve the creation of lithographically-defined binding sites at a preset distance from each other, forming a spatially ordered grid. Electrostatic or covalent coupling with a treated substrate enables single DNA origami placement with nanometer precision exclusively in the size-matched binding sites. These embodiments can form the basis of a quantitative detection platform, including the detection and quantification of biomolecules (e.g., viral DNA). Currently, Electron-Beam Lithography (EBL) forms the backbone of DNA origami placement with nanometer-scale precision. However, there are significant drawbacks to EBL, including expense and specialized training.

In contrast, embodiments of the present disclosure provide a more straightforward, cleanroom-free, and hence, widely accessible DNA origami placement platform that uses a modified nanosphere lithography approach based on nanosphere patterning (NP), as disclosed and described herein. Using a close-packed crystalline monolayer of self-assembled nanospheres as a sacrificial mask, perfectly ordered, easily modifiable, and optically resolvable grids of binding sites on the order of ~100-200 million/cm$^2$ can be created via surface chemical modifications. Subsequent DNA origami placement, combined with in situ amplification of bound viral DNA/RNA, or protein provides an ultra-sensitive quantitative readout from a small sample volume. Additionally, the present disclosure provides a bottom-up approach based on NP that can be easily applied to the fabrication of metal-clad, pre-loaded Zero Mode Waveguides (ZMWs) for single-molecule studies.

Embodiments of the present disclosure provide methods involving bottom-up device fabrication of DNA origami-based quantitative nucleic acid or protein-based disease-detection arrays. In accordance with these methods, highly ordered 2D arrays of single DNA origami binding sites on an approximately 1 cm$^2$ glass chip are provided. These arrays were used to carry out an on-chip isothermal Hybridization Chain Reaction (HCR) reaction, and can facilitate quantitative disease-detection. Additionally, the single molecule arrays of the present disclosure were used to generate ZMWs for DNA sequencing/PAINT experiments by expanding the bottom-up fabrication approach described herein.

Embodiments of the present disclosure provide materials and methods for the fabrication/manufacturing of highly ordered 2D arrays comprising single molecule DNA origami binding sites on an approximately 1 cm$^2$ glass chip. Embodiments of the present disclosure also provide materials and methods for the fabrication/manufacturing of ZMWs using a bottom-up approach for DNA sequencing and PAINT procedures, and the use of these platforms for carrying out the absolute quantification of disease targets.

Example 1—Nanosphere Patterning (NP)

FIGS. 1A-1E include representative schematics of an exemplary workflow for single molecule array fabrication, including nanosphere patterning (NP) processes and DNA origami deposition. Glass coverslips are activated in a plasma cleaner (FIG. 1A), followed by nanosphere monolayer self-assembly (FIG. 1B), surface passivation (FIG. 1C), nanosphere lift-off (FIG. 1D), and DNA origami placement (FIG. 1E). The process described in the workflow schematics of FIGS. 1A-1E was termed nanosphere patterning (NP).

FIGS. 2A-2E include representative images from various stages of a single molecule array fabrication process, including benchtop, cleanroom-free DNA origami placement. Scanning electron microscopy (SEM) (FIG. 2A) and high-tilt SEM (FIG. 2B) images demonstrate hexagonal close-packing (HCP) of a polystyrene nanosphere monolayer; atomic force microscopy (AFM) images demonstrate hexagonal arrays of binding sites (FIG. 2C); DNA origami nanostructures on a PEG-silane background are demonstrated with (inset) a hexagonal arrangement of DNA origami nanostructures; and hexagonal arrangement and multiple DNA origami molecules binding to an HMDS-passivated substrate is demonstrated (FIG. 2E).

Figures 7A, 7B, 7C:
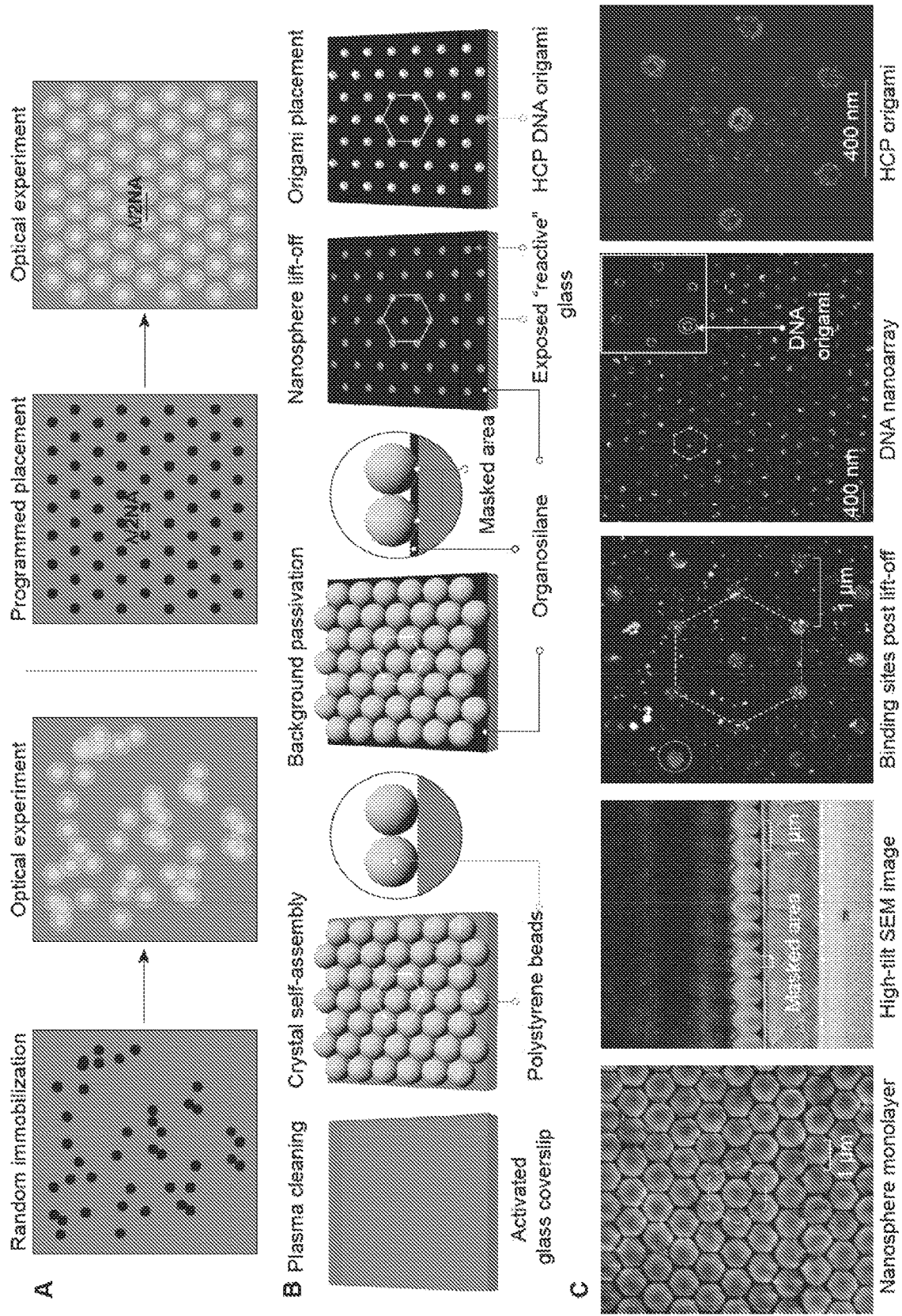
FIGS. 7A-7C show a nanoarray platform. Schema showing the contrast between single molecule experiments in a randomly immobilized fashion compared to deterministic single molecule placement on the DNA origami nanoarray platform (FIG. 7A), and the nanopatterning procedure workflow from plasma cleaning to close-packed crystal self-assembly, to background passivation, nanosphere lift-off, and finally origami placement.

FIGS. 7A-7C include representative schematics and experimental results from an exemplary workflow for single molecule array fabrication, including nanosphere patterning (NP) processes and DNA origami deposition. Schema showing the contrast between single molecule experiments in a randomly immobilized fashion compared to deterministic single molecule placement on the DNA origami nanoarray platform (FIG. 7A), and the nanopatterning procedure workflow from plasma cleaning to close-packed crystal self-assembly, to background passivation (using hexamethyldisilazane), nanosphere lift-off, and finally origami placement (FIG. 7B), and experimental results highlighting optimized single, circular origami placement on nanosphere-defined "binding" sites for digital assays (FIG. 7C).

Figures 8A, 8B, 8C, 8D:
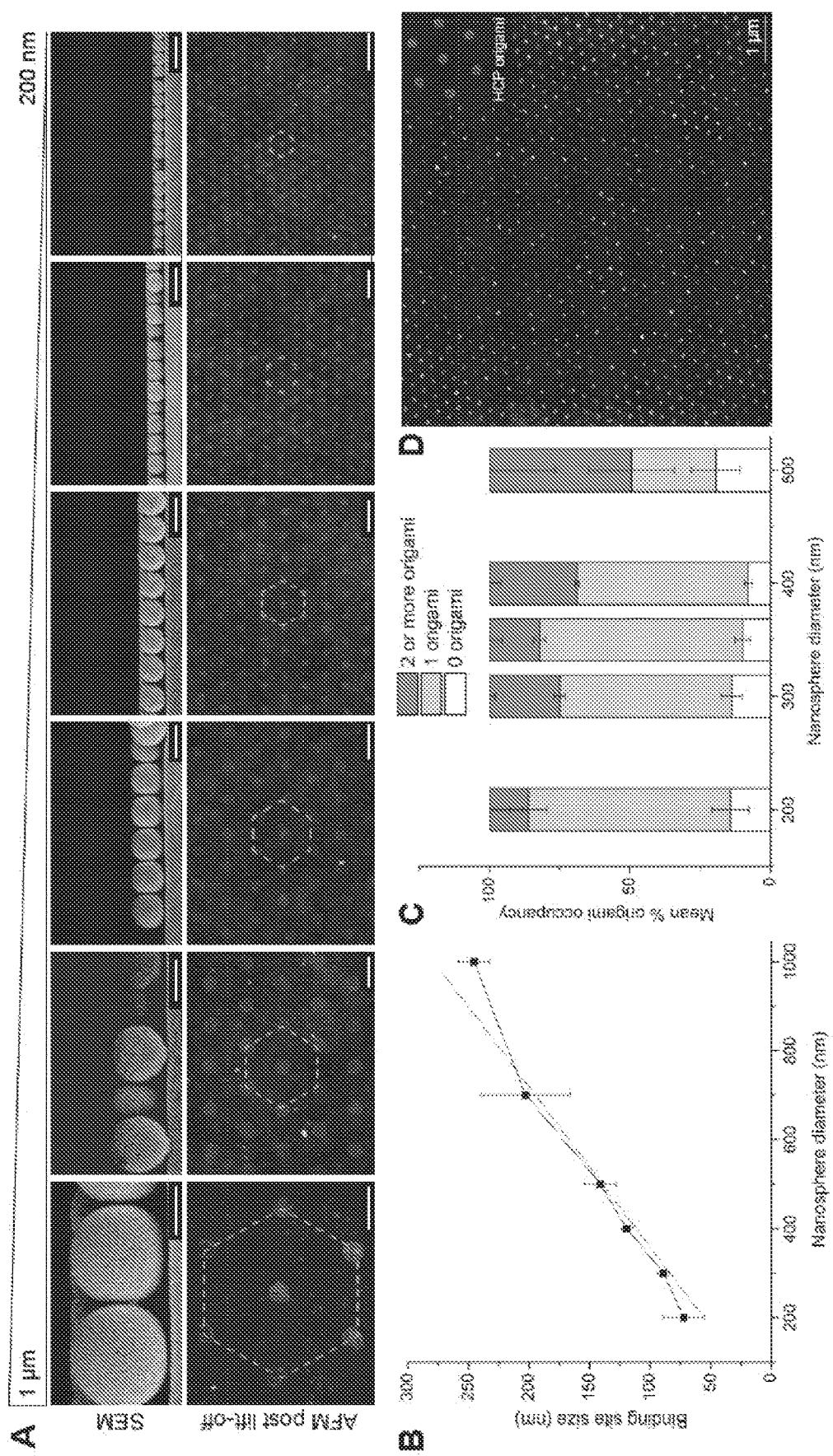
FIGS. 8A-8D show experimental results for process characterization.

FIGS. 8A-D represent experimental results for process characterization. Cross-sectional Scanning Electron Micrographs (top) and corresponding Atomic Force Micrographs (bottom) of nanospheres, and their corresponding binding sites (FIG. 8A). ~94% linear dependence of binding site size on nanosphere diameter (FIG. 8B). Mean occupancy percentage of 0, 1, or more than one origami in binding sites as a function of nanosphere diameter demonstrating non-Poisson statistics of single molecule binding (FIG. 8C). Nanoarray patterning facilitated by an automated washing step using a peristaltic pump to mitigate manual error propagation (FIG. 8D). Scale bars are 500-nm.

Various methods are acceptable for establishing nanosphere monolayer coverage on the surface of an activated glass coverslip, including but not limited to spin-coating, Langmuir-Blodgett based deposition, and tilted drop-casting via solvent evaporation for close-packed monolayer formation (FIG. 2A, FIGS. 7B-7C). SEM imaging under a highly tilted setup revealed the contact area of nanospheres with the glass substrate they were deposited on (FIG. 2B, FIGS. 7B-7C). This area was measured to be 20-30% of the nanosphere diameter. This area of contact acted as a protective mask, decoupling the glass surface directly underneath from any downstream chemical treatment. Nanospheres in a 25% ethanol solution were deposited at a ~45° tilt, and the glass surface was thoroughly dried. A short plasma cleaning step removed any particulate contamination on the surface. A widely available organosilane, hexamethyldisilazane (HMDS), was chosen for vapor deposition of a neutral alkylated group on the activated (silanol-enriched) coverslip, but also demonstrated passivation via PEG-silane (FIG. 2D, FIG. 7C). Thereafter, nanospheres were "lifted-off" (e.g., dissolved) by sonication in water, leaving behind an array of binding sites spatially separated by the diameter of the nanospheres. Binding sites provided access to silanol groups on the glass surface, whereas the bulk of the surface remained passivated. Incubating DNA origami on the surface caused selective binding of the DNA origami to the silanol groups via the formation of Mg++ salt bridges. These initial placement experiments were performed with rectangular origami (80 nm×60 nm). These initial placement experiments were also performed with circular origami (100 nm×100 nm). Alternatively, larger DNA origami created by weaving together multiple scaffolds can enable single binding on large binding sites. In such a case, the larger pitch (center-to-center distance) between binding sites provides for downstream single-molecule imaging applications using standard epi-fluorescence microscopy, Drying artifacts, and spurious binding events have been observed (FIGS. 2D-2E, 7C), but can be mitigated through the exclusion of an ethanol drying step (prescribed for optimal AFM imaging) and extensive washing (e.g., increasing Tween-20 concentration in Tris-HCl buffer), respectively.

Origami aligned themselves on binding sites (to maximize the number of silanol—$Mg^{2+}$-origami bridges) by a process of 2D diffusion once they land on the surface. Numerically matching the binding site and origami geometries was therefore paramount to maximizing single bindings. The relationship between nanosphere diameter and corresponding binding site size was be given by d=kx, where d is the binding site diameter, x is the nanosphere diameter, and k is the scaling co-efficient, i.e. the ratio of nanosphere footprint to its diameter. Observed was a nearly linear correlation using contact AFM-($R^2$=94%, N≥400) post nanosphere lift-off as a means of direct quantification, with k=0.27. Circular, 2-D origami, approximately 100-nm across were synthesized for the purpose of origami binding efficiency characterization. Nanosphere diameters 500-nm resulted in an unfavorable, sub-Poisson limit performance (<37% single occupancy). The highest single origami occupancy values was expected to be around the 300-400 nm nanosphere diameter range owing to the origami and binding site geometries being almost identical to each other (FIG. 8B). A reduction in multiple origami bindings per site with a reduction in nanosphere diameter was expected. The experimental observations were consistent with these predictions and a maximal, 72.4±2.13% single origami occupancy (N≥400) was observed (FIG. 8C) when the origami were 350-nm apart from each other—a pitch that is at the limit of diffraction for a standard microscope, Being an end-point analysis, the measurement statistics likely underestimated the number of single and multiple bindings of origami on the binding sites and were, in fact, a more comprehensive reflection of the fabrication process quality. Only a fractional drop in single binding efficiency was observed in slightly undersized sites (~70-80% of origami diameter) as a result of using 200-nm nanospheres. Variability associated with placement results was attributed, in part, to three tedious manual washing steps (5-minutes each) prior to drying and AFM characterization. To mitigate the effect of operator variability, this washing process was automated and demonstrated ~66% single origami occupancy with this method (FIG. 8D). The setup comprised a peristaltic pump and 3-D printed tube holder for positional alignment between runs without manual intervention.

Example 2—Holliday Junction-Fret, DNA-Paint

Figures 3A, 3B, 3C:
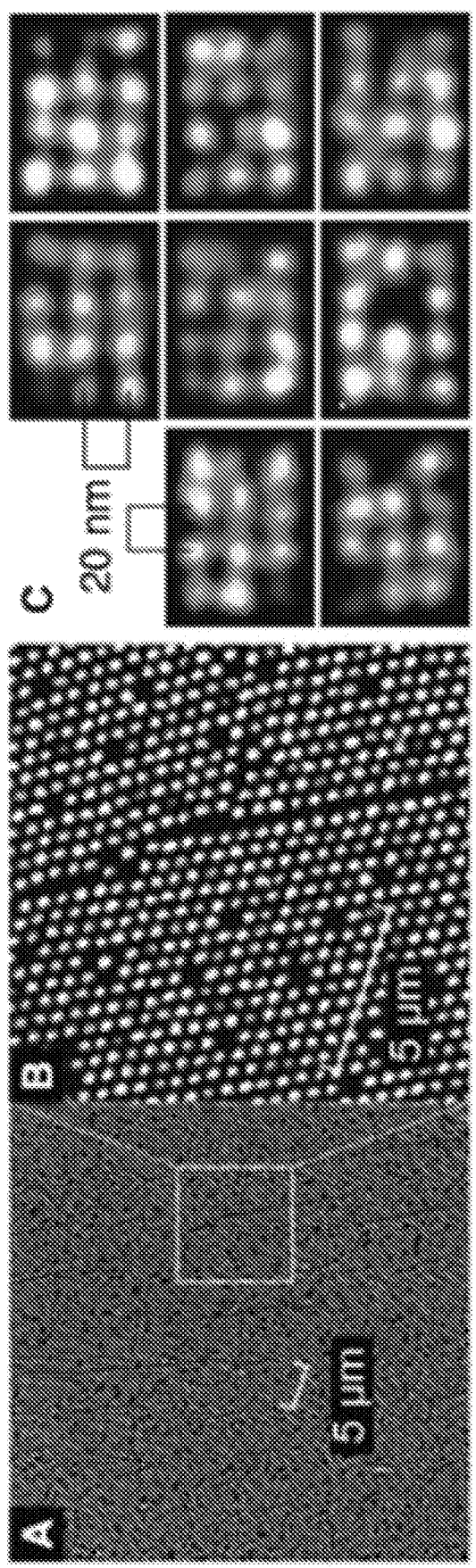
FIGS. 3A-3C include representative images of a single molecule array (2D grid of DNA origami) obtained using DNA points accumulation for imaging in nanoscale topography (DNA-PAINT) on a 500-nm pitch with HMDS background.

Using the single molecule arrays described herein, parallel DNA-PAINT experiments were performed using DNA origami immobilized on the placement substrate. The placement protocol circumvented the use of BSA, BSA-biotin, and Streptavidin treatments for origami immobilization and surface passivation characteristic of traditional DNA-PAINT. Instead, incubation with 0.5% Tween-20 in Tris-HCl buffer (pH 8.35, 40 mM Mg+±) preserved the positions of immobilized origami while passivating the HMDS background further. The PEG moieties in the Tween mitigated background binding of the single-stranded oligonucleotides in solution which were observed to bind readily to a hydrophobic HMDS surface. A typical PAINT procedure can range anywhere between 2-4 hours in data collection time to accumulate an adequate number of localization events at each expected spot on the origami. FIG. 3A includes an example of a PAINT dataset with excellent Signal to Noise Ratio (SNR) coupled with signal localization on the DNA origami bound to NP sites at a 500-nm pitch. Powerful segmentation and drift correction courtesy of a software package, Picasso, were used to resolve the 4×3 configuration of docking strands on several DNA origami molecules.

FIGS. 3A-3C include representative images of a single molecule array (2D grid of DNA origami) obtained using DNA points accumulation for imaging in nanoscale topography (DNA-PAINT) on a 500-nm pitch with HMDS background. FIG. 3A includes an image of 30,000 integrated fluorescence frames collected on a super-resolution microscope; FIG. 3B includes a section of the array showing multiple hexagonal arrangements of DNA origami; and FIG. 3C includes representative 4×3, 20-nm grids of linker strands unraveled post-Picasso processing on a dataset collected using traditional PAINT protocol.

Single molecule arrays of the present disclosure that included DNA origami were amenable to DNA-PAINT super-resolution imaging through the single-stranded DNA molecules attached on one face of the origami (FIG. 3C). DNA-PAINT is a technology currently accessible exclusively by research laboratories with high-end super-resolution microscopes. The rectangular DNA origami included 12 "docking strands" in a 4×3 grid, each at a 20-nm distance from its adjacent strands. Accumulation of transient binding events via fluorescently labelled "imager" strands in solution complementary to docking strands revealed the 20-nm, 4×3 grid of binding sites on each origami.

Figures 9A, 9B, 9C:
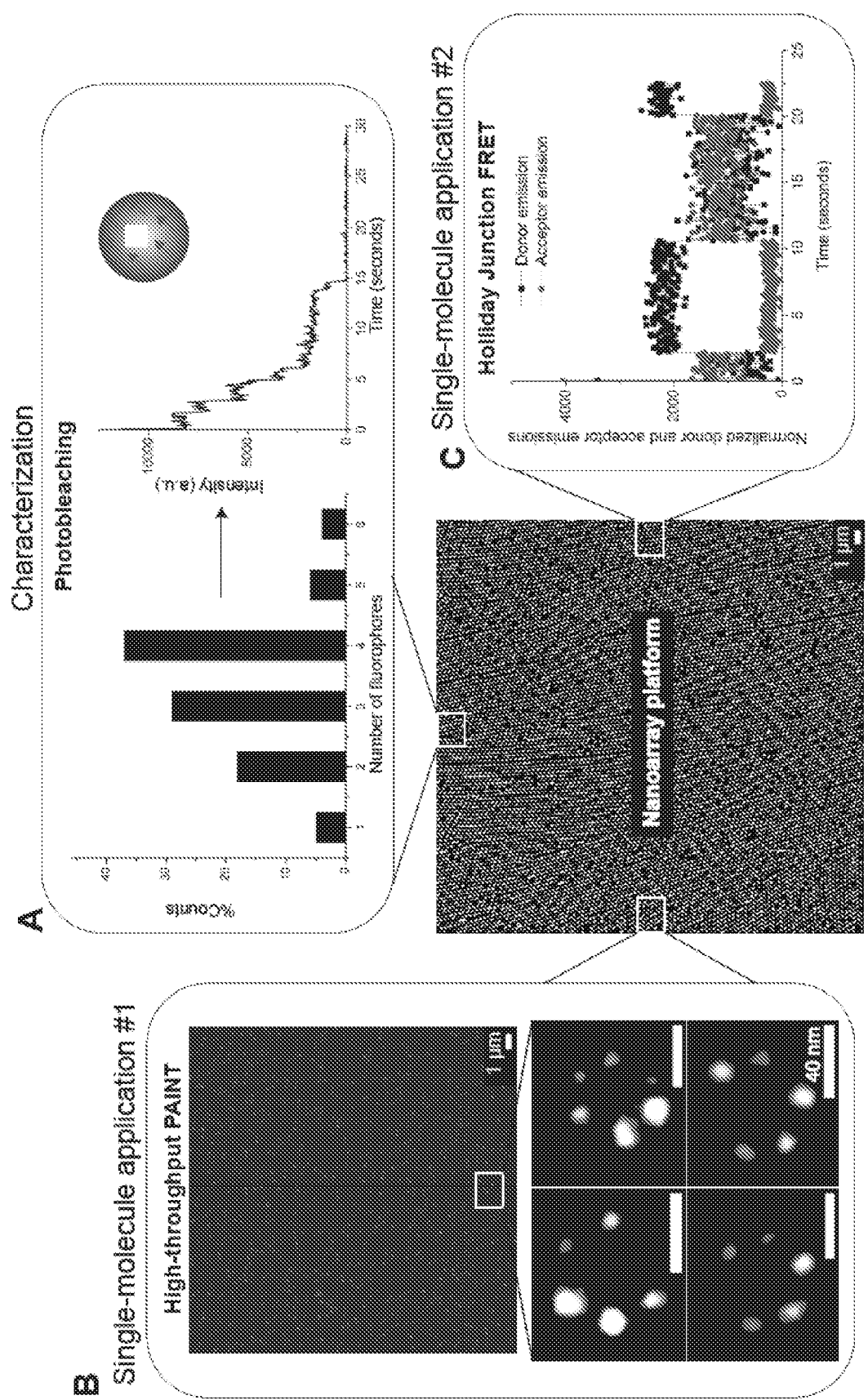
FIGS. 9A-9C show the multi-faceted nature of the nanoarray platform validated through high-throughput single molecule biophysics experiments such as photobleaching (for strand/single molecule conjugation characterization (FIG. 9A), DNA-Points Accumulation for Imaging on the Nanoscale Topography (PAINT) for stochastic super-resolution microscopy of single DNA strands located in a hexagon, 40-nm from each other (FIG. 9B), and Holliday-Junction Forster Resonance Energy Transfer (FRET) for probing single molecule dynamics (FIG. 9C).

FIGS. 9A-9C represent the multi-faceted nature of the nanoarray platform validated through high-throughput single molecule biophysics experiments such as photobleaching (for strand/single molecule conjugation characterization, FIG. 9A), DNA-Points Accumulation for Imaging on the Nanoscale Topography (PAINT) for stochastic super-resolution microscopy of single DNA strands located in a hexagon, 40-nm from each other, and Holliday-Junction Forster Resonance Energy Transfer (FRET) for probing single molecule dynamics (FIG. 9C).

Counting of fluorophore photobleaching events is a standard method of characterizing hybridization efficiency (FIG. 9A). Preliminary photobleaching results indicated ~56% strand conjugation efficiency. Photobleaching, however, has been reported to be experimentally and analytically cumbersome owing, in part, to the complex photophysics of dye molecules. Super-resolution DNA-PAINT has proven to be an effective alternative for quantification of ssDNA but can be stifled by stochasticity associated with biotin-avidin immobilization chemistry routinely used for SME. Single molecule arrays of the present disclosure that included DNA origami were amenable to DNA-PAINT super-resolution imaging through the single-stranded DNA molecules attached on one face of the origami (FIG. 9B). DNA-PAINT is a technology currently accessible exclusively by research laboratories with high-end super-resolution microscopes. The circular DNA origami included 6 "docking strands" in a hexagonal pattern, each at a 40-nm distance from its adjacent strands. Accumulation of transient binding events via fluorescently labelled "imager" strands in solution complementary to docking strands revealed the 40-nm, hexagonal structures of binding sites on each origami. High-density PAINT experiments were performed on patterned substrates with inter-origami pitches of ~400 nm to maintain diffraction-limited resolvability of grids (FIG. 9B). As a second application of high-throughput single-molecule biophysics, kinetics of fluorescent FRET-pairs were extracted. Grid-based experiments comprised HJ strands conjugated to a DNA origami staple strand with a short, 0.5 T spacer sequence for observation of conformational dynamics over time (FIG. 9C). An approximately twenty-fold increase was found in experimental throughput (data density) using the nanoarray platform for DNA-PAINT, and HJ-FRET studies.

Example 3—Self-Assembly and Etching

Figures 4A, 4B, 4C, 4D, 4E, 4F:
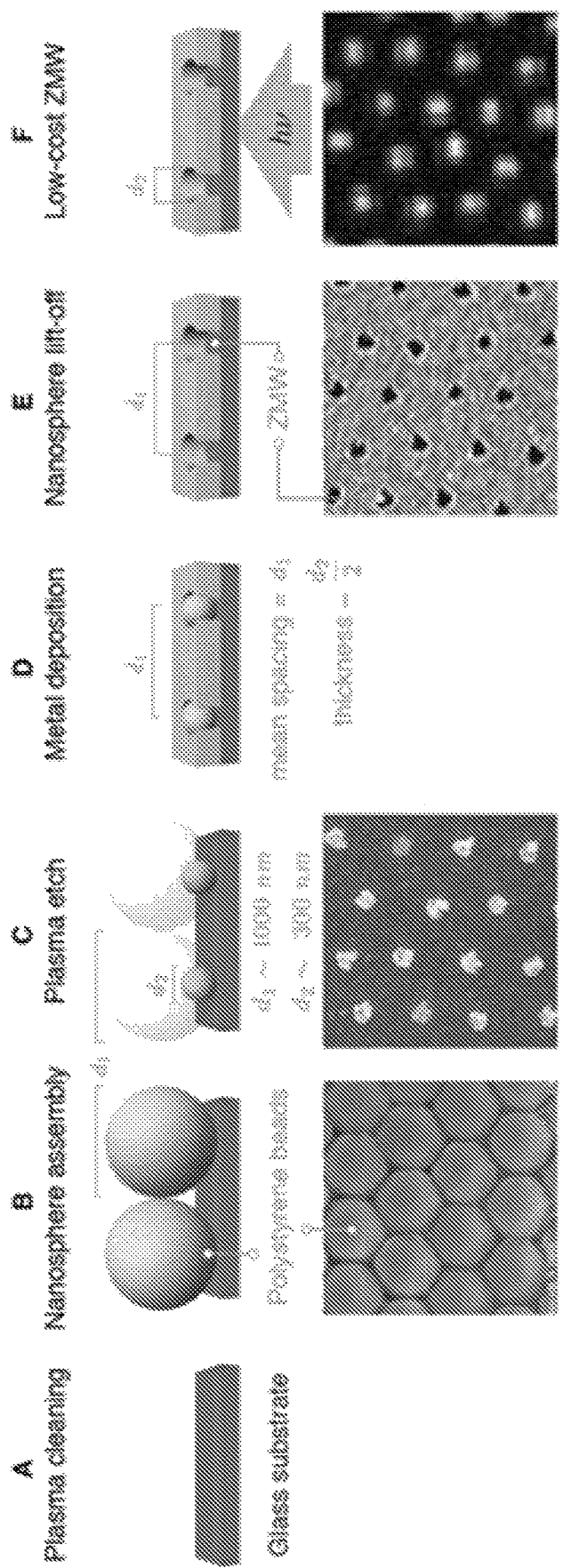
FIGS. 4A-4F include representative schematics and images of an exemplary alternative workflow for single molecule array fabrication, including zero mode waveguide (ZMW) micro-machining using an alternative "self-assemble and etch" method (schematic drawings). The workflow of "self-assemble and etch" includes nanosphere deposition (FIGS. 4A-4B), isotropic etching (FIG. 4C), aluminum deposition (FIG. 4D), and nanosphere lift-off (FIG. 4E). SEM images (FIGS. 4B, 4C, and 4E) and an epi-fluorescence image (FIG. 4F) are shown below their respective workflow schematic.

FIGS. 4A-4F include representative schematics and images of an exemplary alternative workflow for single molecule array fabrication, including zero mode waveguide (ZMW) micro-machining using an alternative "self-assemble and etch" method (schematic drawings). The workflow of "self-assemble and etch" includes nanosphere deposition (FIGS. 4A-4B), isotropic etching (FIG. 4C), aluminum deposition (FIG. 4D), and nanosphere lift-off (FIG. 4E). SEM images (FIGS. 4B, 4C, and 4E) and an epi-fluorescence image (FIG. 4F) are shown below their respective workflow schematic.

While developing the rationale for bottom-up ZMW fabrication on an immobilized DNA origami platform, a parallel approach involving self-assembly and isotropic etching was developed to determine the suitability of nanosphere micromachining for fabricating a hexagonally close-packed grid of point sources of light. This approach would help estimate ZMW diameters and metal layer thicknesses required for adequate light attenuation. This method began with a process similar to the NP technique described above (i.e., tilted drop-casting of nanospheres onto an activated glass coverslip). Nanospheres were then etched isotropically in air plasma at ~18 W, for 70 minutes. Thereafter, a 100 TIM layer of aluminum was deposited onto the substrate, followed by nanosphere lift-off via dissolving in an appropriate solvent solution, or sticky tape. The metal nanoapertures were backlit in transmission mode in epi- as well as TIRF-fluorescence configurations with performances not being radically different. The process workflow is documented in FIGS. 4A-4F. The nanospheres resisted etching past a mean diameter of ~300 nm, and instead started deforming. As these data demonstrate, this size of nanoapertures is adequate for ZMW-like performance. It has been previously reported that: $d_C = 0.586\ \alpha_M$; where $d_C$ is the cut-off diameter for (a perfect conductor as) the cladding material, and $\alpha_M$ is the wavelength of the incident light in the medium of the material filling the ZMW. That is, the cut-off diameter $d_C = 311.75$ nm for 532 nm, and $d_C = 375$ nm for 640 nm incident light.

Example 4—Self-Assembly of Monolayers Using NP on a Chip-Scale

To fabricate the single molecule arrays of the present disclosure, a self-assembled monolayer (SAM) of nanospheres was used as a sacrificial mask. The diameter of the nanospheres dictated the size of each binding site, and the pitch between adjacent binding sites. Nanosphere deposition was carried out via a Langmuir-Blodgett type vertical retraction, a 3-D printer based tilted retraction setup, or controlled evaporation. Both require a monolayer of spheres (in a spreading solvent such as 1-Butanol) to be formed on water. This was followed by deposition of the monolayer onto a hydrophilic glass substrate as it is retracted from the immersion phase (water) to the dispersed/monolayer phase and finally to air. The glass was rendered hydrophilic by bombardment of ions from air plasma generated at high (radio) frequencies.

Alternatively, a method of drop-casting under controlled conditions can be used to form the SAM by depositing a drop of the colloidal mixture onto a hydrophilic glass surface tilted at an angle. Once deposited and dried, a vapor phase or liquid phase chemical passivation step using Hexamethyldisilazane (HMDS) or PEG-silane was used to render the entire surface area of the substrate neutral (i.e., passive). Only the protected reactive silanol groups (from plasma cleaning) in the area of contact between each nanosphere and the substrate carry any form of charge. The nanospheres can then be "lifted-off," or dissolved, by sonication in water to expose the reactive silanol groups under them. This will prime the substrate for selective placement of origami as diagrammed in FIGS. 1A-1E. The surface coverage of nanospheres and the expected coverage of DNA origami, and consequently the number of single, active component carrying sites was determined.

Example 5—DNA Origami Design and Correlation to Binding Site Size

A 2D rectangular DNA origami was used from an already existing origami design for binding site experiments. This design was utilized for downstream demonstration of placement compatibility (via PAINT). Once the DNA origami was assembled and purified using an appropriate (100 kDa) spin-column, it was used for placement on a substrate as described previously. Briefly, using specific experimental parameters including incubation time, pH, Mg++ concentration, and DNA origami concentration, a single origami was bound to the silanol groups with >45% efficiency via the formation of Mg++ bridges, immobilizing the origami on the surface. The binding is sensitive to the binding area available; therefore, the size of the DNA origami and binding area should be correlated. These data demonstrate that the size of nanosphere "footprints" varies with nanosphere diameter. Additionally, DNA origami nanostructures can be designed to circumvent the use of nanospheres close to the diffraction limit of light (without which it would be difficult to resolve two adjacent spots under a standard light microscope). Passivation and placement conditions were optimized to obtain mostly single DNA origami binding of approximately 140 million origami/$cm^2$ (>45% single binding efficiency) (i.e., approximately 140 million distinctly addressable ZMW-budding and (optically resolvable) nucleic acid amplification and detection spots on a 1 $cm^2$ glass chip). DNA origami placement can also be optimized with respect to Mg++ concentration using various surface chemistry approaches such as CIES (carboxyethylsilanetriol), and buffer conditions.

A circular DNA origami was used from an already existing origami design for binding site experiments. This design was utilized for downstream demonstration of placement compatibility (via PAINT). Once the DNA origami was assembled and purified using an appropriate (100 kDa) spin-column, it was used for placement on a substrate as described previously. Briefly, using specific experimental parameters including incubation time, pH, Mg concentration, and DNA origami concentration, a single origami was bound to the silanol groups with >75% efficiency via the formation of Mg++ bridges, immobilizing the origami on the surface. The binding is sensitive to the binding area available; therefore, the size of the DNA origami and binding area should be correlated. These data (FIGS. 8B-8C) demonstrate that the size of nanosphere "footprints" varied with nanosphere diameter. Additionally, DNA origami nanostructures can be designed to circumvent the use of nanospheres close to the diffraction limit of light (without which it would be difficult to resolve two adjacent spots under a standard light microscope). Passivation and placement conditions were optimized to obtain mostly single DNA origami binding of approximately 140 million origami/$cm^2$ (>75% single binding efficiency) (i.e., approximately 140 million distinctly addressable ZMW-budding and (optically resolvable) nucleic acid amplification and detection spots on a 1 $cm^2$ glass chip). DNA origami placement can also be optimized with respect to Mg++ concentration using various surface chemistry approaches such as CTES (carboxyethylsilanetriol), and buffer conditions.

Example 6—Bottom-Up ZMW Fabrication Paradigm

Figures 5A, 5B, 5C, 5D, 5E:
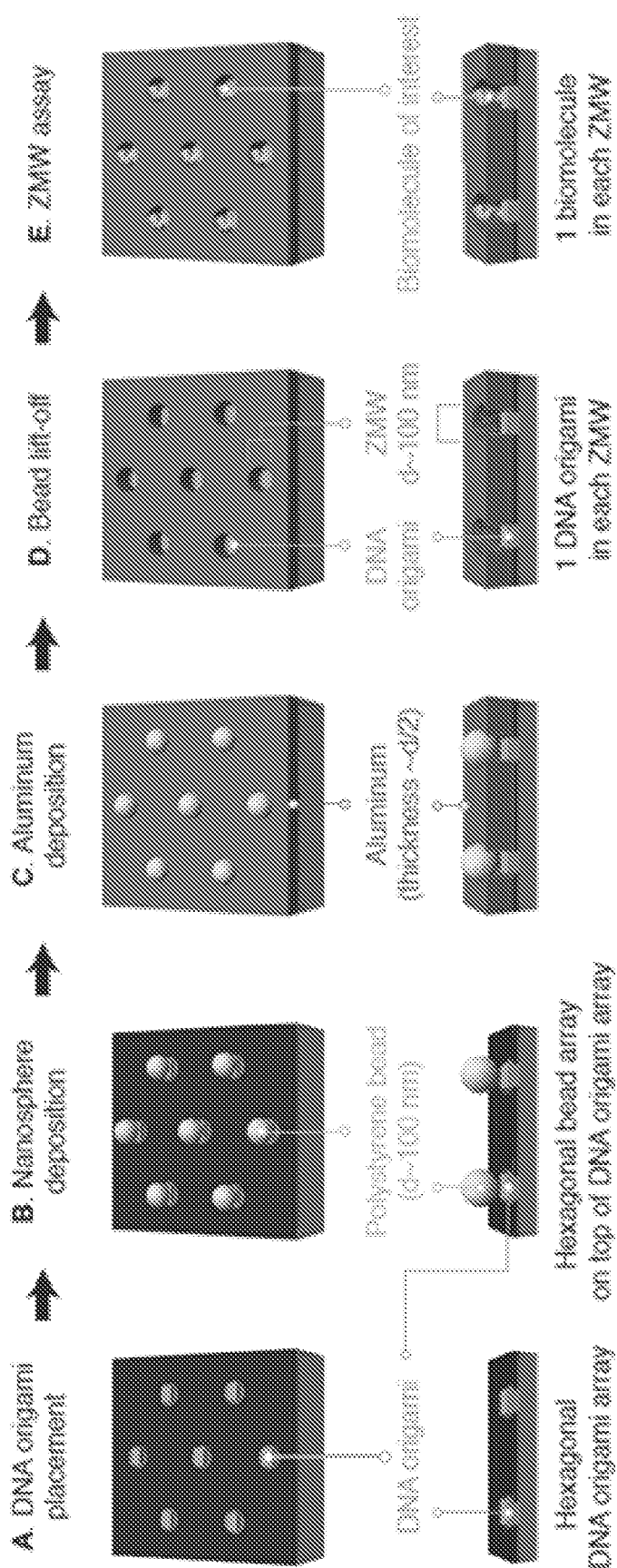
FIGS. 5A-5E include representative schematics of a bottom-up single molecule array fabrication process. A functionalized 2D DNA origami grid (FIG. 5A) was obtained, and nanospheres were deposited and linked to DNA origami molecules using EDC-NHS, electrostatic, or Biotin-Streptavidin coupling (FIG. 5B), followed by aluminum deposition on the nanospheres (FIG. 5C), and lift-off (FIG. 5D).

An immobilized origami grid created with the NP technique described herein (FIGS. 5A-5E) can be used to obtain >75%, non-Poisson limited single-molecule (e.g., DNA origami) occupancy per binding site will form the backbone of bottom-up ZMW fabrication. For example, in one embodiment, an immobilized origami grid created with the NP technique described herein (FIG. 8C) obtained >72%, non-Poisson limited single-molecule (e.g., DNA origami) occupancy per binding site will form the backbone of bottom-up ZMW fabrication. The origami can be modified to incorporate several amine-terminated linker strands on the side facing-up. Incubation with EDC-NHS activated, amine-reactive carboxylated nanospheres can result in nanospheres covalently binding to the immobilized aminated-DNA origami. Each origami can be configured to bind exactly one nanosphere. Once bound, this nanosphere can be used as a sacrificial mask layer to deposit a chosen thickness of aluminum (FIGS. 5C-5D). Post metal-deposition, the nanosphere can be dissolved in Tetrahydrofuran, or another such solvent in which the origami is stable (and will remain immobilized on the glass surface; FIG. 5D). A second, possibly more straightforward approach to nanosphere-origami binding is that of electrostatically attaching the carboxylated nanospheres to aminated-origami under the right pH, and Mg++ concentration conditions. A third alternative is to attach streptavidin-coated nanospheres to biotinylated strands extending from DNA origami.

Embodiments of the single molecule arrays of the present disclosure may also include a high-density grid of metal nanoapertures that will serve as ZMWs (FIG. 5E). However, unlike traditionally top-down fabricated ZMW devices, >75% of these ZMW nanoapertures can be present with built-in single DNA origami. For example, in one embodiment, >72% of these ZMW nanoapertures were present with built-in single DNA origami. These fabrication methods overcome Poisson-limited loading of single-molecules via the NP process, and can recruit other biological molecules of interest for single-molecule experiments in the μM-to-mM concentration regime. Thus, the single-molecule DNA origami baseplate array can build-up ZMWs while also being built into them, overcoming the long-standing Poisson-limited single-molecule occupancy in such devices.

In some embodiments, at least a 2:1 (sacrificial layer: deposited layer can be maintained for clearance for complete nanosphere lift-off (dissolving). AFM, and SEM can enable structural characterization of this process. The fabrication of ZMWs in the range of 50-200 nm can generally be targeted, and characterization of the optical performance of each corresponding grid in terms of light attenuation, and Point Spread Functions (PSFs) can be performed. The pitch of the immobilized origami grid can be varied between 300-1000 nm for these experiments to test the performance of the ZMWs as point sources of light at the limit of diffraction (~270 nm). In some embodiments, the DNA origami is configured to be positioned with the right side up, presenting the active components for nanosphere binding. This can be facilitated by incorporating PEG/Poly-T or similar entropic "brushes" on the top side which will repel the reactive groups on the binding site, ensuring orientation of origami.

Example 7—DNA Sequencing and Paint Functionality

Embodiments of the single molecule arrays of the present disclosure may also include a single DNA polymerase (conjugated to a "handle" DNA strand) immobilized on built-in origami, post-ZMW fabrication around these origami. Multiple washing steps can be performed to wash the excess, unbound polymerases away. Thereafter, the template strand to be sequenced, and fluorescent deoxyribo-nucleoside triphosphate (dNTPs), can be introduced and hybridized, and the DNA sequencing reaction can occur with real-time fluorescence events being captured.

In another set of experiments, ZMW nanoarrays can be incubated with a high concentration of imager strands complementary to a 4×3 array of linker strands extending from the built-in single origami in every ZMW. The higher imager concentration can increase the number of blinking/binding events per site per unit of time, thereby reducing the acquisition time by 2-3 orders of magnitude through shorter exposure time. The resolution of the 20-nm spaced (4×3) grid can confirm access to strands in the ZMWs, and consequently form a functional bottom-up device fabrication platform. Sensor characterization for PAINT experiments can involve characterization of the percentage resolution of observed probes with respect to expected probes.

Example 8—In Situ Isothermal Nucleic Acid Amplification Through Hybridization Chain Reaction (HCR)

FIGS. 6A-6E and FIG. 10A include a schematic illustration of the proposed DNA/RNA hybridization reaction (HCR) using commercially available strands to setup a chain reaction for linear amplification of a bound nucleic acid target sequence. The strands comprise a "probe or initiator" which has two sub-sections: one complementary to a single-stranded linker extending from the immobilized origami baseplate, and another to a sub-section of one out of two fluorescently-labelled hairpin strands. Once bound to the DNA origami and in contact with the complementary region on the selected hairpin from the solution, the initiator triggers opening of the hairpin. This reaction is fueled by the second hairpin, which binds another sub-section of the first hairpin, and opens up, thus commencing a cyclical strand-displacement process. This continues until all the strands in solution have been exhausted. By binding an initiator to exactly one complementary strand on each immobilized origami, approximately similar site-specific intensities of real-time and terminally integrated fluorescence can be obtained.

Figures 6A, 6B, 6C, 6D, 6E, 6F, 6G:
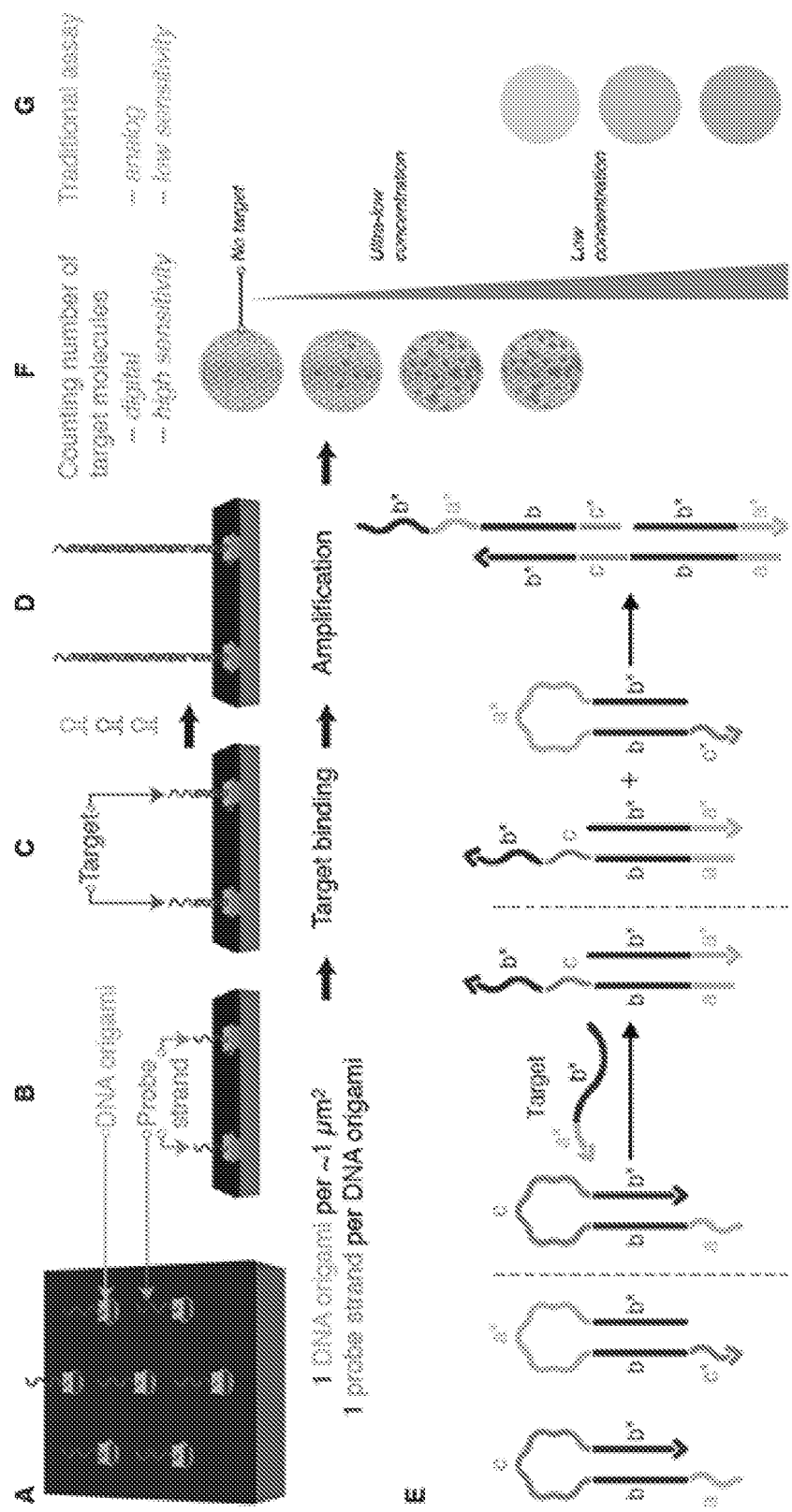
FIGS. 6A-6C include representative schematics of in situ hybridization chain reaction (HCR) carried out using a single molecule array comprising a 2D DNA origami grid. A functionalized 2D DNA origami grid (FIG. 6A) was obtained, hosting disease-targeting probe strands (FIG. 6B) and probe strands that bind target strands-of-interest (FIGS. 6D-6E). Enzyme-free HCR based on the introduction of metastable hairpins results in a fluorescent signal for quantifying trapped viral particles; quantification comparison between the proposed digital (FIG. 6F) and more conventional analog (FIG. 6G) assays.

In some embodiments, the initiator strand models a disease target DNA or RNA sequence. Each fluorescent spot can be equivalent to a single binding event, enabling straightforward quantification of molecules over the entire glass substrate. To maintain origami immobilization, the reaction conditions can be maintained at a suitable pH and Mg++ concentration. Both DNA and RNA HCR can be performed to draw parallels with DNA and RNA disease targets. An alternative in situ amplification technique, compatible with chip-based platforms is RCA. Embodiments of these methods can enable digital quantification of molecules (FIG. 6F) instead of a qualitative "analog" output (FIG. 6G). The process of using known strands can additionally enable the establishment of a microscope detection threshold. Consequently, a concentration and temporal threshold for the strands used can be identified, and reaction progression can be monitored.

Figure 10A:
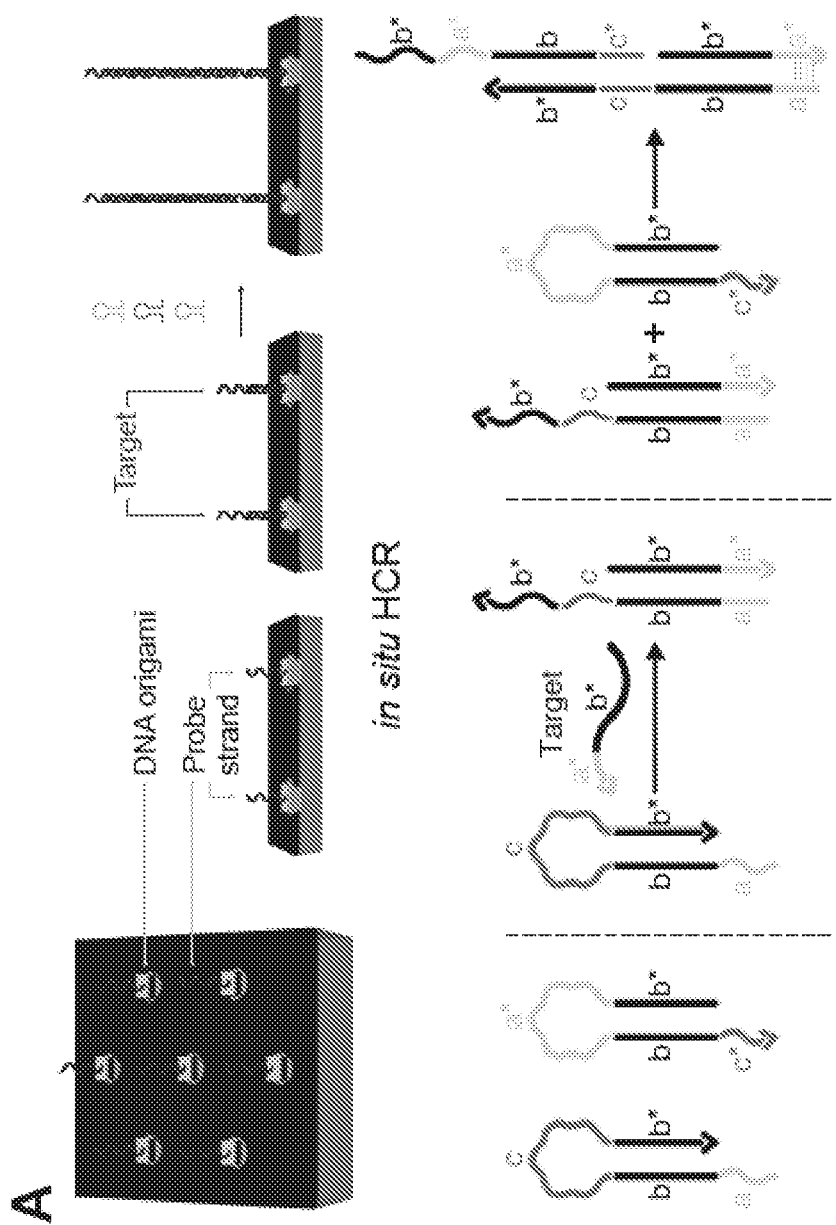
FIGS. 10A-10D show In situ, enzyme-free amplification for low-cost digital target detection.
Figure 10B:
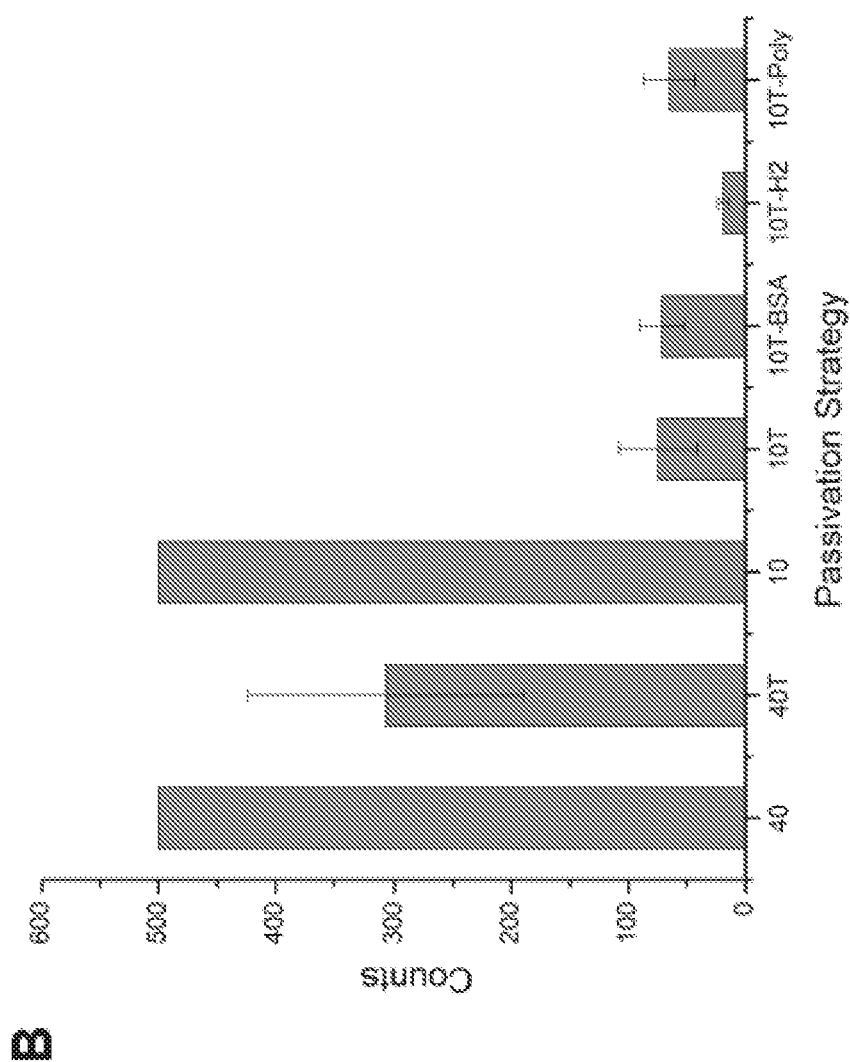
Figure 10C:
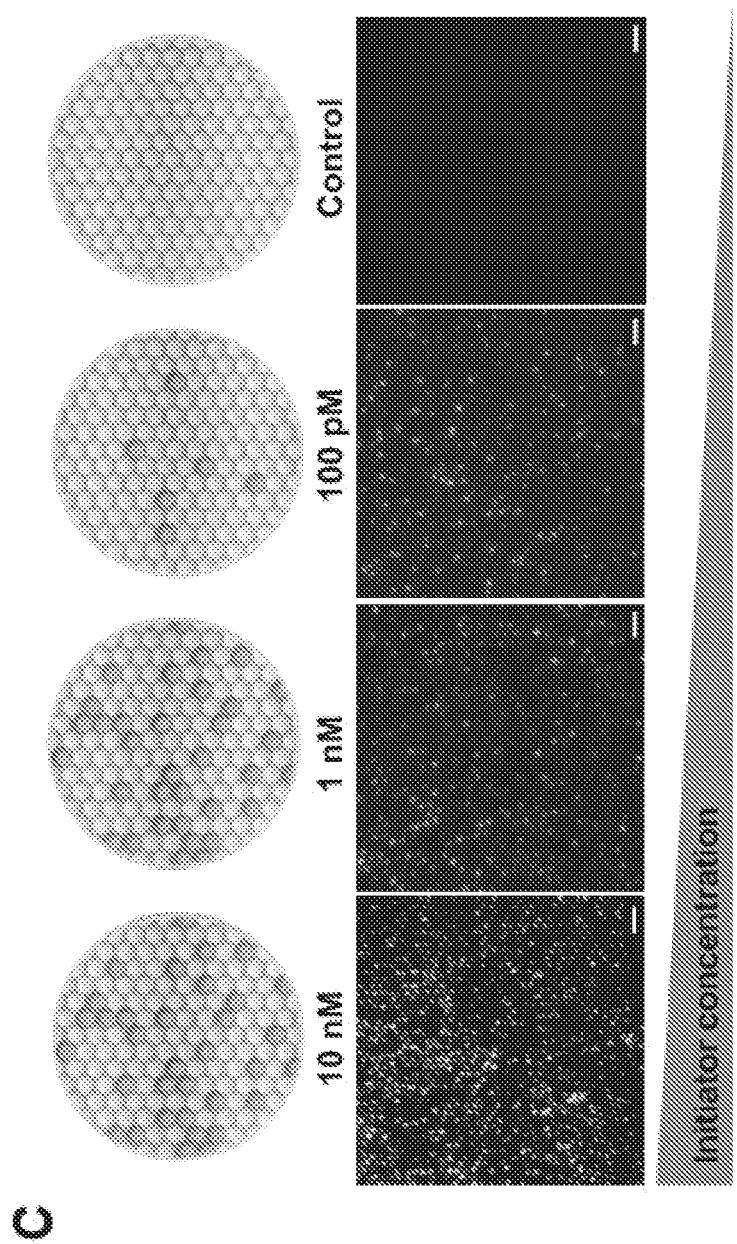

Surface-based hybridization reactions were extremely susceptible to nonspecifically bound molecules confounding overall analysis of results. With photon budget being the major currency of such experiments, background noise, or false positives can be detrimental if not addressed adequately, especially in digital-diagnostic applications. Several strategies were tested, and it was observed that the $H_2$ "flood"-based competitive binding strategy with 10 mM $Mg^{2+}$-Tween provided optimum passivation of the glass surface, thereby boosting Signal to Noise Ratio (SNR). FIG. 10B shows the optimal surface passivation through competitive excess strand binding (~200× excess) for minimal false positives. FIG. 10C shows the serial dilution of synthetic target species indicating a ~10-100 pM limit of detection. A consequent ~10 pM detection limit (FIG. 10C) was observed using purified, synthetic targets.

Figure 10D:
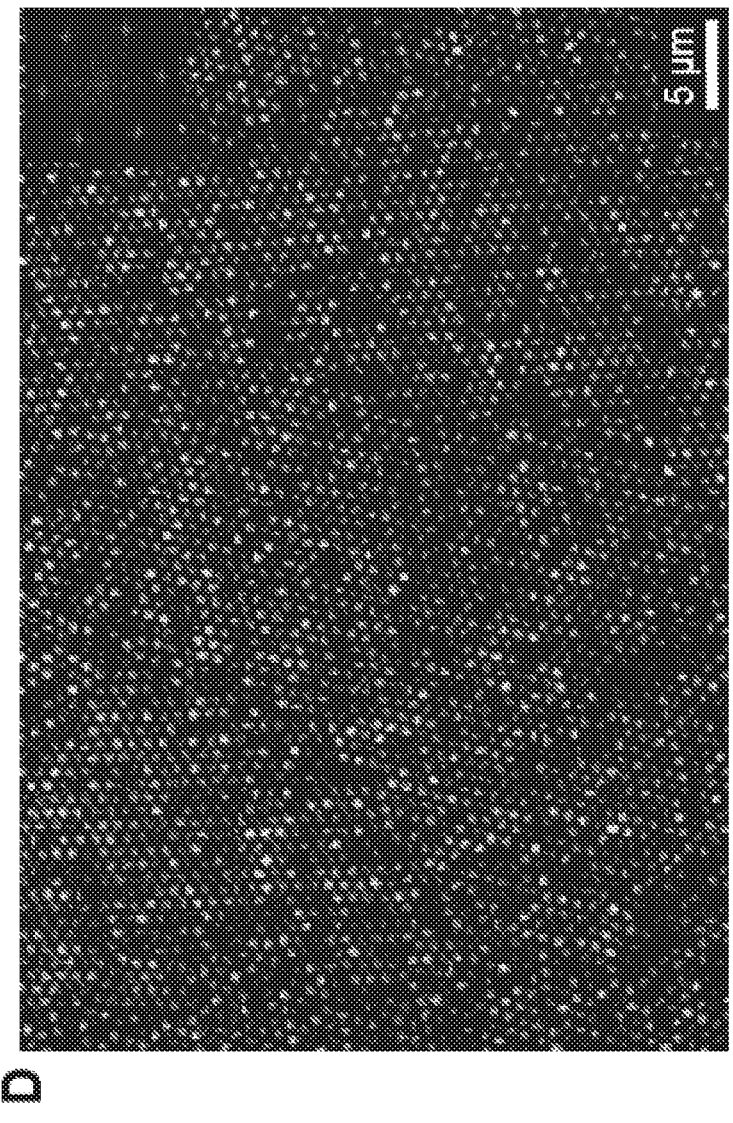

Disease diagnosis in low-resource settings demands the development of easily accessible and portable imaging setups. A low-cost imaging setup was developed for portable digital assays (FIG. 10D).

Figures 11A, 11B:
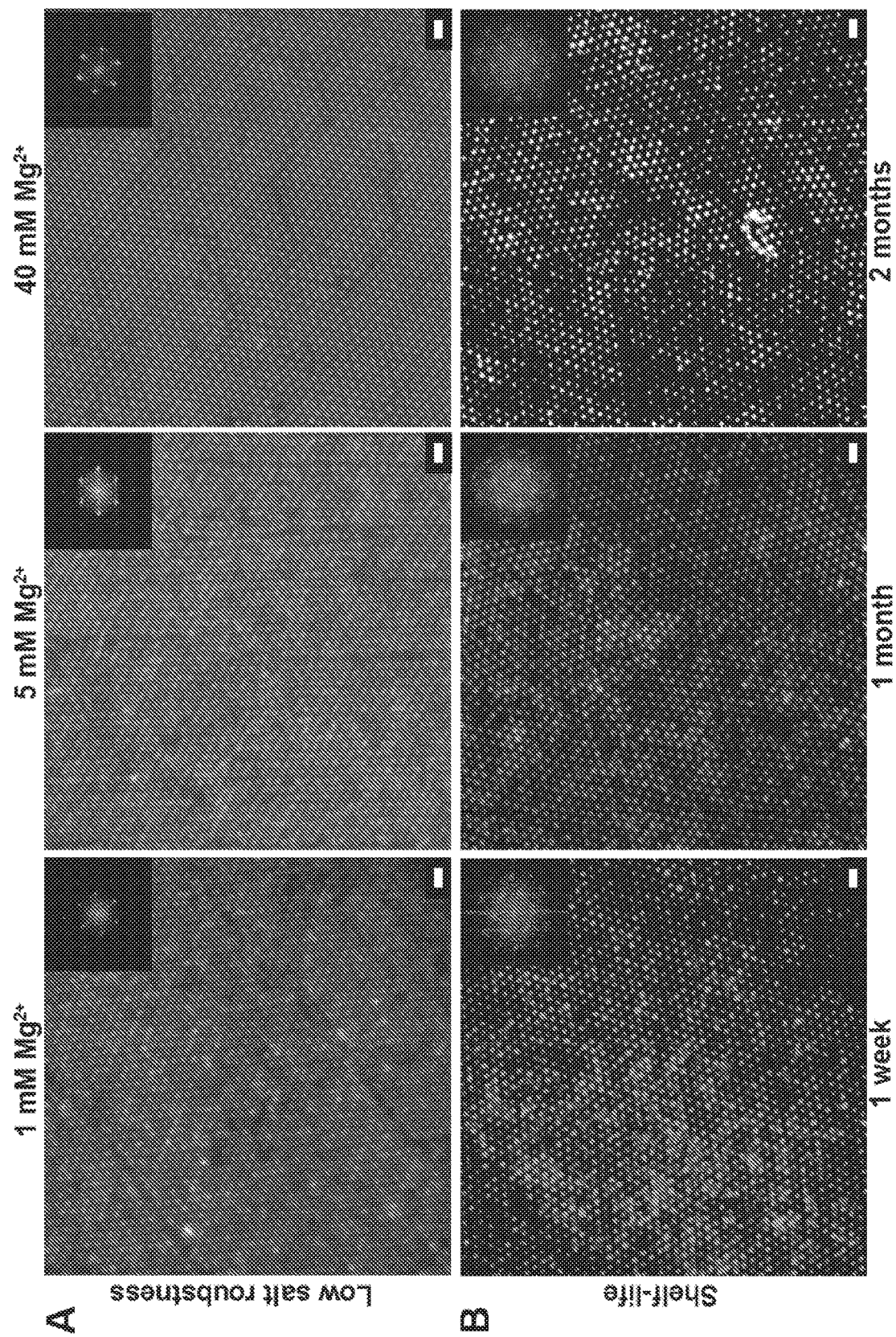
FIGS. 11A-11B show platform robustness validation. Experimental results demonstrating robustness of the nanoarray platform under low salt conditions for single molecule experiment compatibility (FIG. 11A), and a long shelf-life of several months under ambient conditions without special storage requirements (FIG. 11B).

FIGS. 11A-11B show platform robustness validation. Experimental results are shown demonstrating robustness of the nanoarray platform under low salt conditions for single molecule experiment compatibility (FIG. 11A), and a long shelf-life of several months under ambient conditions without special storage requirements (FIG. 11B).

Example 9—HCR-Based Biosensing of Disease Targets for Detection and Quantification Once in situ amplification and quantification of nucleic acids have been demonstrated, a disease can be targeted. Such diseases can include but are not limited to AAV (Adeno-associated virus), H5N3 (Avian influenza), BFDV (Budgerigar fledgling disease virus), BTV (Bluetongue virus), Ebola, Enterovirus 71, GHPV (Goose hemorrhagic polyoma virus), HBV (Hepatitis B virus), HCV (Hepatitis C virus), HDV (Hepatitis δ virus), HEV (Hepatitis E virus), HIV, HPV (Human papillomavirus), IBDV (Infectious bursal disease virus), Influenza A, Influenza A H1N1, Influenza A H3N2, polymavirus, Margurg, MS2, IPCV (Indian peanut clump virus), NDV (Newcastle disease virus), No (Norovirus), Nv (Norwalk virus), PhMV (Physalis mottle virus), Polymavirus, PPV (Porcine parvovirus), RHDV (Rabbit hemorrhagic disease virus), Rotavirus. SARS, SIV (Simian immunodeficiency virus), SV40 (Simian virus 40), SVDV (Swine vesicular disease virus), and the like. Probes/initiator strands specific to these disease targets, as well as others, can be designed and immobilized on the DNA origami arrays of the present disclosure. An exemplary workflow for HCR amplification is depicted by the schematic in FIG. 6E and FIG. 10A.

Various features and advantages of the invention are set forth in the following claims.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

For reasons of completeness, various aspects of the invention are set out in the following numbered clauses, as well as the following claims:

Clause 1, A single molecule array comprising: an activated silanol-enriched glass substrate; a organosilane base layer deposited onto the glass substrate, wherein the organosilane base layer comprises a plurality of regularly spaced binding sites; and an artificial nucleic acid nanostructure layer comprising a plurality of individual nucleic acid molecules bound to silanol groups on the glass substrate within the plurality of regularly spaced binding sites.

Clause 2. The array of clause 1, wherein the glass substrate is treated with a plasma cleaner.

Clause 3. The array of clause 1 or clause 2, wherein the glass substrate is a transparent glass chip about 1 cm2.

Clause 4. The array of any of clauses 1-3, wherein the organosilane base layer is deposited onto the glass substrate using surface passivation, and wherein the organosilane base layer comprises at least one of hexaniethyldisilazane (HMDS), PEG-silane, CTES and HMDS, trimethylsilyl (TMS), and amino-terminated silane (Aminopropylsilatrane).

Clause 5. The array of any of clauses 1-4, wherein the binding sites have diameters formed by a plurality of regularly spaced removable nanospheres deposited on and in contact with the glass substrate prior to application of the organosilane base layer.

Clause 6. The array of any of clauses 1-5, wherein the regularly spaced removable nanospheres are polystyrene beads.

Clause 7. The array of any of clauses 1-6, wherein the plurality of regularly spaced binding sites are about 80 nm to about 200 nm in diameter.

Clause 7A. The array of any of clauses 1-6, wherein the plurality of regularly spaced binding sites are about 80 nm to about 200 nm, about 80 nm to about 150 nm, about 80 nm to about 100 nm, about 90 nm to about 200 nm, about 90 nm to about 150 nm, about 90 nm to about 100 nm, about 100 nm to about 200 nm, about 100 nm to about 150 nm, or about 150 nm to about 200 nm in diameter.

Clause 7B. The array of any of clauses 1-6, wherein the plurality of regularly spaced binding sites are about 80 nm, about 85 nm, about 90 nm, about 95 nm, about 100 nm, about 105 nm, about 110 nm, about 120 nm, about 130 nm, about 140 nm, about 150 nm, about 170 nm, about 180 nm, about 190 nm, or about 200 nm in diameter.

Clause 8. The array of any of clauses 1-7, wherein the binding sites number from about 100 million per $cm^2$ to about 200 million per $cm^2$.

Clause 8A. The array of any of clauses 1-7, wherein the binding sites number from about 100 million per $cm^2$ to about 200 million per $cm^2$, about 125 million per $cm^2$ to about 200 million per $cm^2$, 150 million per $cm^2$ to about 200 million per $cm^2$, 175 million per $cm^2$ to about 200 million per $cm^2$, about 100 million per $cm^2$ to about 175 million per $cm^2$, about 12.5 million per $cm^2$ to about 175 million per $cm^2$, 150 million per $cm^2$ to about 175 million per $cm^2$, 175 million per cm2 to about 200 million per cm2, about 100 million per $cm^2$ to about 150 million per $cm^2$, or about 125 million per $cm^2$ to about 150 million per $cm^2$.

Clause 8B. The array of any of clauses 1-7, wherein the binding sites number are about about 100 million per $cm^2$, about 110 million per $cm^2$, about 120 million per $cm^2$, about 130 million per $cm^2$, about 140 million per $cm^2$, about 150 million per $cm^2$, about 160 million per $cm^2$, about 170 million per $cm^2$, about 180 million per $cm^2$, about 190 million per $cm^2$, or about 200 million per $cm^2$.

Clause 9. The array of any of clauses 1-8, wherein the plurality of individual nucleic acid molecules in the artificial nucleic acid nanostructure layer are further conjugated to a plurality of removable polystyrene beads, which upon removal, form a plurality of zeromode waveguide (ZMW) nanoapertures.

Clause 10. The array of any of clauses 1-9, wherein the plurality of individual nucleic acid molecules contained within the plurality of binding sites comprise individual DNA origami nanostructures.

Clause 11. The array of any of clauses 1-10, wherein the individual DNA origami nanostructures are generally circular, generally square, or generally rectangular in shape, and range from about 50 nm to about 200 nm in width and about 50 nm to about 200 nm in length.

Clause 11A. The array of any of clauses 1-10, wherein the individual DNA origami nanostructures are generally circular, generally square, or generally rectangular in shape, and range from about 50 nm to about 200 nm, about 50 nm to about 150 nm, about 50 nm to about 100 nm in width, about 50 nm to about 75 nm, about 75 nm to about 200 nm, about 75 nm to about 150 nm, about 75 nm to about 100 nm in width, about 100 nm to about 200 nm, about 100 nm to about 150 nm, or about 150 nm to about 200 nm in width.

Clause 11B. The array of any of clauses 1-10, wherein the individual DNA origami nanostructures are generally circular, generally square, or generally rectangular in shape, and have a width of about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm.

Clause 11C. The array of any of clauses 1-10, wherein the individual DNA origami nanostructures are generally circular, generally square, or generally rectangular in shape, and range about 50 nm to about 200 nm, about 50 nm to about 150 nm, about 50 nm to about 100 nm in width, about 50 nm to about 75 nm, about 75 nm to about 200 nm, about 75 nm to about 150 nm, about 75 nm to about 100 nm in width, about 100 nm to about 200 nm, about 100 nm to about 150 nm, or about 150 nm to about 200 nm in length.

Clause 11D. The array of any of clauses 1-10, wherein the individual DNA origami nanostructures are generally circular, generally square, or generally rectangular in shape, and have a length of about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 mm.

Clause 12. The array of any of clauses 1-11, further comprising a metallic layer deposited onto the organosilane base layer, wherein the metallic layer comprises a plurality of zeromode waveguide (ZMW) nanoapertures.

Clause 13. The array of any of clauses 1-12, wherein the metallic layer comprises at least one of aluminum, silver, gold, and chromium.

Clause 14. The array of any of clauses 1-13, wherein the ZMW nanoapertures in the metallic layer have diameters formed by a plurality of regularly spaced removable nanospheres deposited on and in contact with the plurality of individual nucleic acid molecules prior to application of the metallic layer.

Clause 15. A single molecule array comprising: an activated silanol-enriched glass substrate; a metallic base layer deposited onto the glass substrate, wherein the metallic base layer comprises a plurality of regularly spaced nanoapertures; and an artificial nucleic acid nanostructure layer comprising a plurality of individual nucleic acid molecules contained within each nanoaperture and bound to silanol groups on the glass substrate; wherein the nanoapertures have diameters formed by a plurality of regularly spaced removable nanospheres deposited on and in contact with the glass substrate prior to application of the metallic base layer.

Clause 16. The array of clause 15, wherein the metallic layer comprises at least one of aluminum, silver, gold, and chromium.

Clause 17. A method for manufacturing a single molecule array, the method comprising: depositing a plurality of removable nanospheres onto an activated silanol-enriched glass substrate; depositing an organosilane base layer onto the glass substrate and the plurality of nanospheres; removing the plurality of nanospheres to form a plurality of binding sites in the organosilane base layer in regions where the plurality of nanospheres contacted the glass substrate; and depositing an artificial nucleic acid nanostructure layer comprising a plurality of individual nucleic acid molecules onto the organosilane base layer, wherein the plurality of individual nucleic acid molecules are contained within the plurality of binding sites, and are bound to silanol groups on the glass substrate.

Clause 18. The method of clause 17, wherein the glass substrate is treated with a plasma cleaner prior to deposition.

Clause 19. The method of clause 17 or clause 18, wherein depositing the plurality of removable nanospheres comprises at least one of: i) spin-coating; ii) Langmuir-Blodgett based deposition; or iii) tilted drop-casting via solvent evaporation.

Clause 20. The method of any of clauses 17-19, wherein depositing the organosilane base layer onto the glass substrate and the plurality of nanospheres comprises at least one of: i) vapor deposition of hexamethyldisilazane (HMDS); or ii) liquid phase deposition of PEG-silane.

Clause 21. The method of any of clauses 17-20, wherein removing the plurality of nanospheres comprises sonication.

Clause 22. The method of any of clauses 17-21, wherein depositing the artificial nucleic acid nanostructure layer comprises incubation with DNA origami, wherein individual DNA origami molecules selectively bind to silanol groups on the glass substrate via Mg++ bridges.

Clause 23. A method of performing points accumulation for imaging in nanoscale topology (PAINT) using the single molecule array of any of clauses 1-16.

Clause 24. A method of performing in situ nucleic acid amplification through hybridization chain reaction (HCR) using the single molecule array any of clauses 1-16.

Clause 25. A method of performing hybridization chain reaction (HCR)-based biosensing for detecting or diagnosing a disease target using the single molecule array any of clauses 1-16.

What is claimed is:

1. A single molecule array comprising:
   an activated silanol-enriched glass substrate;
   an organosilane base layer deposited onto the glass substrate, wherein the organosilane base layer comprises a plurality of regularly spaced binding sites; and
   an artificial nucleic acid nanostructure layer comprising a plurality of individual nucleic acid molecules, wherein the plurality of individual nucleic acid molecules comprise individual DNA origami nanostructures bound to silanol groups on the glass substrate via $Mg^{2+}$ salt bridges within the plurality of regularly spaced binding sites, wherein the individual DNA origami nanostructures are further conjugated to a plurality of removable polystyrene beads, which upon removal, form a plurality of individual nanoapertures containing individual DNA origami nanostructures.

2. The array of claim 1, wherein the glass substrate is treated with a plasma cleaner.

3. The array of claim 1, wherein the glass substrate is a transparent glass chip about 1 $cm^2$.

4. The array of claim 1, wherein the organosilane base layer is deposited onto the glass substrate using surface passivation, and wherein the organosilane base layer comprises at least one of hexamethyldisilazane (HMDS), PEG-silane, CTES+HMDS, trimethylsilyl (TMS), amino-terminated silane (Aminopropylsilatrane-APS) in binding sites, covalent immobilization via amide or isourea bond on binding sites.

5. The array of claim 1, wherein the binding sites have diameters formed by a plurality of regularly spaced removable nanospheres deposited on and in contact with the glass substrate prior to application of the organosilane base layer.

6. The array of claim 1, wherein the plurality of regularly spaced binding sites are about 80 nm to about 200 nm in diameter.

7. The array of claim 1, wherein the binding sites number from about 100 million per $cm^2$ to about 200 million per $cm^2$.

8. The array of claim 1, wherein the individual DNA origami nanostructures are generally circular, generally square, or generally rectangular in shape, and range from about 50 nm to about 200 nm in width and about 50 nm to about 200 nm in length.

9. The array of claim 1, further comprising a metallic layer deposited onto the organosilane base layer, wherein the metallic layer comprises a plurality of zeromode waveguide (ZMVV) nanoapertures.

10. The array of claim 9, wherein the ZMW nanoapertures in the metallic layer have diameters formed by a plurality of regularly spaced removable nanospheres deposited on and in contact with the plurality of individual nucleic acid molecules prior to application of the metallic layer.

11. A single molecule array comprising:
    an activated silanol-enriched glass substrate;
    a metallic base layer deposited onto the glass substrate, wherein the metallic base layer comprises a plurality of regularly spaced ZMW nanoapertures and at least one of aluminum, silver, gold, and chromium, or combinations thereof; and
    an artificial nucleic acid nanostructure layer comprising a plurality of individual nucleic acid molecules comprised of individual DNA origami nanostructures contained within each ZMW nanoaperture and bound to silanol groups on the glass substrate via $Mg^{2+}$ salt bridges;

wherein the ZMW nanoapertures have diameters formed by a plurality of regularly spaced removable nanospheres deposited on and in contact with the individual DNA origami nanostructures prior to application of the metallic base layer.

12. A bottom-up method for manufacturing a single molecule array, the method comprising:

depositing an artificial nucleic acid nanostructure layer comprising a plurality of individual nucleic acid molecules onto an activated silanol-enriched glass substrate, wherein the plurality of individual nucleic acid molecules comprise individual DNA origami nanostructures selectively bound to silanol groups on the glass substrate via $Mg^{2+}$ salt bridges;

depositing a plurality of removable nanospheres onto the activated silanol-enriched glass substrate and the individual DNA origami nanostructures, wherein the plurality of removable nanospheres are conjugated to the individual DNA origami nanostructures;

depositing an organosilane base layer onto the glass substrate and the plurality of nanospheres; and removing the plurality of nanospheres to form a plurality of binding sites in the organosilane base layer in regions where the plurality of nanospheres contacted the individual DNA origami nanostructures;

wherein the plurality of binding sites comprise individual nanoapertures containing individual DNA origami nanostructures.

13. The method of claim 12, wherein the glass substrate is treated with a plasma cleaner prior to deposition.

14. The method of claim 12, wherein depositing the plurality of removable nanospheres comprises at least one of: (i) spin-coating; (ii) Langmuir-Blodgett based deposition; or (iii) tilted drop-casting via solvent evaporation.

15. The method of claim 12, wherein depositing the organosilane base layer onto the glass substrate and the plurality of nanospheres comprises at least one of: (i) vapor deposition of hexamethyldisilazane (HMDS); or (ii) liquid phase deposition of PEG-silane.

16. The method of claim 12, wherein removing the plurality of nanospheres comprises sonication.

\* \* \* \* \*